US012588844B2

(12) United States Patent
Feldman et al.

(10) Patent No.: US 12,588,844 B2
(45) Date of Patent: *Mar. 31, 2026

(54) ANALYTE SENSORS AND SENSING METHODS FEATURING DUAL DETECTION OF GLUCOSE AND KETONES

(71) Applicant: Abbott Diabetes Care Inc., Alameda, CA (US)

(72) Inventors: Benjamin J. Feldman, Berkeley, CA (US); Tianmei Ouyang, Saratoga, CA (US); Stephen M. Oja, Reno, NV (US); Lam Tran, Danville, CA (US); Hyun Cho, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,072

(22) Filed: Dec. 19, 2022

(65) Prior Publication Data

US 2023/0121769 A1 Apr. 20, 2023

Related U.S. Application Data

(63) Continuation of application No. 16/774,835, filed on Jan. 28, 2020.

(Continued)

(51) Int. Cl.

*A61B 5/1486* (2006.01)
*A61B 5/145* (2006.01)
*A61L 31/04* (2006.01)

(52) U.S. Cl.

CPC ...... *A61B 5/14865* (2013.01); *A61B 5/14532* (2013.01); *A61B 5/14546* (2013.01); *A61L 31/041* (2013.01)

(58) Field of Classification Search

CPC ............ A61B 5/14865; A61B 5/14532; A61B 5/14546; A61L 31/041

See application file for complete search history.

(56) References Cited

U.S. PATENT DOCUMENTS 4,321,123 A 3/1982 Nakamura et al.
4,721,677 A 1/1988 Clark
(Continued)

FOREIGN PATENT DOCUMENTS

CN 1735375 A 2/2006
CN 101849180 B 8/2017
(Continued)

OTHER PUBLICATIONS

U.S. Appl. No. 16/774,835, filed Jan. 28, 2020.
(Continued)

*Primary Examiner* — Alex M Valvis
*Assistant Examiner* — Anna Roberts
(74) *Attorney, Agent, or Firm* — Sterne, Kessler, Goldstein & Fox P.L.L.C.

(57) ABSTRACT

Glucose and ketones may be dysregulated singularly or concurrently in certain physiological conditions and may be advantageously assayed together using an analyte sensor capable of detecting both analytes. Certain analyte sensors capable of dual detection may comprise a first working electrode and a second working electrode, a ketones-responsive active area disposed upon a surface of the first working electrode, a glucose-responsive active area comprising a glucose-responsive enzyme disposed upon a surface of the second working electrode, a membrane having a first portion overcoating the ketones-responsive active area and a second portion overcoating the glucose-responsive active area, in which the first portion and the second portion have different compositions. The ketones-responsive active area comprises (Continued)

an enzyme system comprising at least two enzymes that are capable of acting in concert to facilitate detection of ketones.

18 Claims, 15 Drawing Sheets

Related U.S. Application Data

(60) Provisional application No. 62/884,869, filed on Aug. 9, 2019, provisional application No. 62/797,566, filed on Jan. 28, 2019.

(56) References Cited

U.S. PATENT DOCUMENTS 5,262,035 A 11/1993 Gregg et al.
5,264,105 A 11/1993 Gregg et al.
5,322,063 A 6/1994 Allen et al.
5,356,786 A 10/1994 Heller et al.
5,593,852 A 1/1997 Heller et al.
5,696,314 A 12/1997 McCaffrey et al.
5,783,056 A 7/1998 Hampp et al.
5,792,621 A 8/1998 Verostko et al.
5,820,551 A 10/1998 Hill et al.
5,965,105 A 10/1999 Rayalu et al.
5,965,106 A 10/1999 Pomato et al.
6,071,391 A 6/2000 Gotoh et al.
6,121,009 A 9/2000 Heller et al.
6,134,461 A 10/2000 Say et al.
6,175,752 B1 1/2001 Say et al.
6,241,863 B1 6/2001 Monbouquette
6,284,478 B1 9/2001 Heller et al.
6,377,894 B1 4/2002 Deweese et al.
6,503,381 B1 1/2003 Gotoh et al.
6,514,460 B1 2/2003 Fendrock
6,514,718 B2 2/2003 Heller et al.
6,541,216 B1 4/2003 Wilsey et al.
6,560,471 B1 5/2003 Heller et al.
6,579,690 B1 6/2003 Bonnecaze et al.
6,600,997 B2 7/2003 Deweese et al.
6,605,200 B1 8/2003 Mao et al.
6,605,201 B1 8/2003 Mao et al.
6,654,625 B1 11/2003 Say et al.
6,676,816 B2 1/2004 Mao et al.
6,736,957 B1 5/2004 Forrow et al.
6,746,582 B2 6/2004 Heller et al.
6,881,551 B2 4/2005 Heller et al.
6,932,894 B2 8/2005 Mao et al.
6,946,299 B2 9/2005 Neel et al.
7,090,756 B2 8/2006 Mao et al.
7,299,082 B2 11/2007 Feldman et al.
7,501,053 B2 3/2009 Karinka et al.
7,520,970 B2 4/2009 Sato et al.
7,563,588 B2 7/2009 Gao et al.
7,754,093 B2 7/2010 Forrow et al.
7,811,231 B2 10/2010 Jin et al.
7,822,557 B2 10/2010 Chen et al.
8,106,780 B2 1/2012 Goodnow
8,268,143 B2 9/2012 Liu et al.
8,435,682 B2 5/2013 Heller
8,444,834 B2 5/2013 Liu et al.
8,545,693 B2 10/2013 Mccoll et al.
8,761,857 B2 6/2014 Feldman et al.
8,911,908 B2 12/2014 Sakai et al.
9,290,839 B2 3/2016 Wang et al.
9,775,549 B2 10/2017 Ouyang et al.
9,914,952 B2 3/2018 Ouyang et al.
9,927,386 B2 3/2018 Wang et al.
9,983,161 B2 5/2018 Feldman et al.
10,022,076 B2 7/2018 Hoss et al.
10,136,816 B2 11/2018 Bernstein et al.
10,201,301 B2 2/2019 Heller et al.
10,702,193 B2 7/2020 Simpson et al.
11,091,788 B2 8/2021 Ouyang et al.
2001/0003045 A1 6/2001 Davis et al.
2003/0042137 A1 3/2003 Mao et al.
2003/0050547 A1 3/2003 Lebel et al.
2003/0068666 A1 4/2003 Zweig
2003/0100821 A1 5/2003 Heller et al.
2004/0061232 A1 4/2004 Shah et al.
2005/0148832 A1 7/2005 Reghabi et al.
2005/0215871 A1 9/2005 Feldman et al.
2006/0004272 A1 1/2006 Shah et al.
2006/0076236 A1 4/2006 Shah et al.
2006/0257996 A1 11/2006 Simpson et al.
2007/0007132 A1 1/2007 Mao et al.
2007/0027385 A1 2/2007 Brister et al.
2007/0042377 A1 2/2007 Gao et al.
2007/0095661 A1 5/2007 Wang et al.
2007/0131547 A1 6/2007 Nomoto et al.
2007/0213611 A1 9/2007 Simpson et al.
2007/0235331 A1 10/2007 Simpson et al.
2007/0270672 A1 11/2007 Hayter
2007/0289881 A1* 12/2007 Forrow .................. C12Q 1/006 435/287.1
2008/0179187 A1 7/2008 Ouyang et al.
2008/0319295 A1 12/2008 Bernstein et al.
2009/0166194 A1 7/2009 Sato et al.
2009/0294306 A1* 12/2009 Feldman .............. G01N 27/301 205/792
2010/0185070 A1 7/2010 Brister et al.
2010/0198034 A1 8/2010 Thomas et al.
2010/0213057 A1 8/2010 Feldman et al.
2010/0230285 A1 9/2010 Hoss et al.
2010/0267161 A1 10/2010 Wu et al.
2010/0268043 A1 10/2010 Yodfat et al.
2010/0324392 A1 12/2010 Yee et al.
2010/0326842 A1 12/2010 Mazza et al.
2011/0039165 A1 2/2011 Sugiyama et al.
2011/0046467 A1 2/2011 Simpson et al.
2011/0065008 A1 3/2011 Nakagawa et al.
2011/0120865 A1 5/2011 Bommakanti et al.
2011/0124993 A1 5/2011 Bommakanti et al.
2011/0124994 A1 5/2011 Bommakanti et al.
2011/0126188 A1 5/2011 Bernstein et al.
2011/0213057 A1 9/2011 Fenn et al.
2011/0213225 A1 9/2011 Bernstein et al.
2011/0256024 A1 10/2011 Cole et al.
2011/0257495 A1 10/2011 Hoss et al.
2012/0132525 A1* 5/2012 Liu ..................... C07F 15/0026 525/327.1
2012/0138484 A1 6/2012 Bommakanti et al.
2012/0150005 A1 6/2012 Hoss et al.
2012/0157801 A1 6/2012 Hoss et al.
2012/0181189 A1 7/2012 Merchant
2012/0186997 A1 7/2012 Li et al.
2012/0245447 A1 9/2012 Karan et al.
2012/0283537 A1 11/2012 Petisce et al.
2012/0296186 A1 11/2012 Ouyang et al.
2012/0323098 A1 12/2012 Moein et al.
2013/0059212 A1 3/2013 Kusumegi et al.
2013/0116524 A1 5/2013 Cole et al.
2013/0131478 A1 5/2013 Simpson et al.
2013/0211219 A1* 8/2013 Coppeta ............. A61B 5/14532 600/347
2013/0231542 A1 9/2013 Simpson et al.
2013/0245412 A1 9/2013 Rong et al.
2013/0324820 A1 12/2013 Petillo et al.
2014/0054171 A1 2/2014 Feldman et al.
2014/0127728 A1 5/2014 Wilsey
2014/0176338 A1 6/2014 He et al.
2014/0262776 A1 9/2014 Martin et al.
2014/0262777 A1 9/2014 Zhao et al.
2015/0038814 A1 2/2015 Staib et al.
2015/0076004 A1 3/2015 Gerber et al.
2015/0207796 A1 7/2015 Love et al.
2016/0045147 A1* 2/2016 Ouyang ............. A61B 5/14532 600/309
2016/0319232 A1 11/2016 Noritomi et al.
2016/0328991 A1* 11/2016 Simpson ............ G09B 19/0092
2016/0345882 A1 12/2016 Wu et al.
2016/0354542 A1 12/2016 Ward et al.
2016/0355862 A1 12/2016 Deng et al.
2017/0156652 A1 6/2017 Qiang et al.

(56) References Cited

U.S. PATENT DOCUMENTS

| | | | |
|---|---|---|---|
| 2017/0191958 | A1 | 7/2017 | Gerber et al. |
| 2017/0202491 | A1 | 7/2017 | Heller et al. |
| 2017/0315077 | A1 | 11/2017 | Rao et al. |
| 2017/0319111 | A1 | 11/2017 | Simpson et al. |
| 2018/0014766 | A1 | 1/2018 | Ouyang et al. |
| 2018/0116604 | A1 | 5/2018 | Newberry |
| 2018/0275088 | A1 | 9/2018 | Huff et al. |
| 2019/0004005 | A1 | 1/2019 | Oja et al. |
| 2019/0024130 | A1 | 1/2019 | Ouyang et al. |
| 2019/0125230 | A1 | 5/2019 | Feldman |
| 2019/0125619 | A1 | 5/2019 | Zeutzius et al. |
| 2019/0271658 | A1 | 9/2019 | Haneda et al. |
| 2019/0274598 | A1 | 9/2019 | Scott et al. |
| 2019/0320947 | A1 | 10/2019 | Chen et al. |
| 2020/0069226 | A1 | 3/2020 | Hahn et al. |
| 2020/0237275 | A1 | 7/2020 | Feldman et al. |
| 2020/0237276 | A1 | 7/2020 | Oja et al. |
| 2020/0237277 | A1 | 7/2020 | Ouyang et al. |
| 2020/0241015 | A1 | 7/2020 | Ouyang et al. |
| 2021/0137431 | A1 | 5/2021 | Oja et al. |
| 2022/0056500 | A1 | 2/2022 | Ouyang et al. |
| 2022/0168727 | A1 | 6/2022 | Baldwa |
| 2022/0386910 | A1 | 12/2022 | Oja et al. |
| 2022/0389475 | A1 | 12/2022 | Ouyang et al. |
| 2022/0395202 | A1 | 12/2022 | Ouyang et al. |
| 2022/0396820 | A1 | 12/2022 | Ouyang et al. |
| 2023/0054564 | A1 | 2/2023 | Ouyang et al. |
| 2023/0080107 | A1 | 3/2023 | Ouyang et al. |
| 2023/0118818 | A1 | 4/2023 | Feldman et al. |
| 2023/0119512 | A1 | 4/2023 | Feldman et al. |
| 2023/0121101 | A1 | 4/2023 | Feldman et al. |
| 2023/0121367 | A1 | 4/2023 | Feldman et al. |
| 2023/0122702 | A1 | 4/2023 | Feldman et al. |
| 2023/0123384 | A1 | 4/2023 | Feldman et al. |
| 2023/0128038 | A1 | 4/2023 | Feldman et al. |
| 2024/0247297 | A1 | 7/2024 | Ouyang et al. |
| 2024/0350047 | A1 | 10/2024 | Oja et al. |
| 2025/0221643 | A1 | 7/2025 | Ouyang et al. |
| 2025/0261884 | A1 | 8/2025 | Oja et al. |

FOREIGN PATENT DOCUMENTS

| | | | | |
|---|---|---|---|---|
| CN | 113164106 | A | 7/2021 | |
| EP | 0990706 | A1 | 4/2000 | |
| EP | 3394252 | A1 | 10/2018 | |
| EP | 3414325 | A1 | 12/2018 | |
| EP | 3597765 | A1 | 1/2020 | |
| EP | 4084689 | A1 | 11/2022 | |
| GB | 2067764 | A | 7/1981 | |
| JP | 2001506742 | A | 5/2001 | |
| JP | 2007510155 | A | 4/2007 | |
| JP | 2007290504 | A | 11/2007 | |
| JP | 2010517054 | A | 5/2010 | |
| JP | 2010530790 | A | 9/2010 | |
| JP | 2011136186 | A | 7/2011 | |
| JP | 2013504053 | A | 2/2013 | |
| JP | 2014503080 | A | 2/2014 | |
| JP | 2014160024 | A | 9/2014 | |
| JP | 2015198960 | A | 11/2015 | |
| JP | 2018029983 | A | 3/2018 | |
| JP | 2022172249 | A | 11/2022 | |
| WO | WO-2003056319 | A2 | 7/2003 | |
| WO | WO-2005040404 | A1 | 5/2005 | |
| WO | WO-2008041984 | A1 | 4/2008 | |
| WO | WO-2009105337 | A2 | 8/2009 | |
| WO | WO-2010030912 | A1 | 3/2010 | |
| WO | WO-2011030093 | A1 * | 3/2011 | ............ G01N 27/26 |
| WO | WO-2012100130 | A1 | 7/2012 | |
| WO | WO-2015150263 | A1 | 10/2015 | |
| WO | WO-2015195352 | A1 | 12/2015 | |
| WO | WO-2016025064 | A1 | 2/2016 | |
| WO | WO-2016174456 | A1 | 11/2016 | |
| WO | WO-2016174458 | A1 | 11/2016 | |
| WO | WO-2017151952 | A1 | 9/2017 | |
| WO | WO-2018067235 | A1 | 4/2018 | |
| WO | WO-2018106129 | A1 | 6/2018 | |
| WO | WO-2019006413 | A1 | 1/2019 | |

OTHER PUBLICATIONS

U.S. Appl. No. 16/774,909, filed Jan. 28, 2020.

U.S. Appl. No. 16/774,841, filed Jan. 28, 2020.

U.S. Appl. No. 16/582,583, filed Sep. 25, 2019.

International Search Report and Written Opinion for International Application No. PCT/US2020/015365, mailed on May 28, 2020, 14 pages.

International Search Report and Written Opinion for International Application No. PCT/US2020/015400, mailed on Apr. 9, 2020, 14 pages.

International Search Report and Written Opinion for International Application No. PCT/2020/015321, mailed on Apr. 9, 2020, 14 pages.

International Search Report and Written Opinion for International Application No. PCT/US2019/052942, mailed on Nov. 28, 2020, 17 pages.

Guiseppi-Elie et al., "Design of Subcutaneous Implantable Biochip for Monitoring of Glucose and Lactate," IEEE Sensors Journal, 5(3):345-355, Jun. 1, 2005.

Pundir, C.S., et al., "Biosensing Methods for Determination of Creatine: A Review," Biosens Bioelectron., 126:707-724, Nov. 19, 2018.

Cardosi, M., et al., "Amperometric Glucose Sensors for Whole Blood Measurement Based on Dehydrogenase Enzymes," Dehydrogenases, InTech (Nov. 2012).

Office Action mailed Apr. 18, 2022 in U.S. Appl. No. 16/774,835, 24 pages.

Office Action mailed Jun. 2, 2022 in U.S. Appl. No. 16/774,909, 13 pages.

Office Action mailed Jun. 24, 2022 in U.S. Appl. No. 16/774,841, 10 pages.

Office Action mailed Sep. 17, 2021 in U.S. Appl. No. 16/774,835, 21 pages.

Office Action mailed Dec. 21, 2022, in U.S. Appl. No. 16/774,909, 13 pages.

Office Action mailed Nov. 25, 2022, in U.S. Appl. No. 17/151,274, 13 pages.

Office Action mailed Sep. 1, 2022, in U.S. Appl. No. 16/582,583, 20 pages.

Office Action mailed Nov. 16, 2022 in U.S. Appl. No. 16/774,841, 10 pages.

Shi, G., et al., "The study of Nafion/zanthine oxidase/Au colloid chemically modified biosensor and its application in the determination of hypoxanthine in myocardial cells in vivo," Analyst, 127(3):396-400 (Mar. 2002).

Mueller, S., et al., "The GOX/CAT system: A novel enzymatic method to independent control hydrogen peroxidase and hypoxia in cell culture," Adv Med Sci., 54(2):121-135 (Dec. 2009).

Burmeister, J., et al., "Self-Referencing Ceramic-Based Multisite Microelectrodes for Detection and Elimination of Interferences from the Measurement of L-Glutamate and Other Analytes," Anal Chem., 73(5):1037-1042 (Mar. 2001).

Monteiro, T., et al., "Construction of effective disposable biosensors for point of care testing of nitrite," Talanta., 142:246-251 (Sep. 2015).

Office Action mailed Mar. 2, 2023 in U.S. Appl. No. 16/774,835, 14 pages.

Office Action mailed Apr. 19, 2023, in U.S. Appl. No. 16/582,583, 18 pages.

Office Action mailed Oct. 3, 2023, in U.S. Appl. No. 16/582,583, 21 pages.

Office Action mailed Sep. 12, 2023, in U.S. Appl. No. 16/774,835, 16 pages.

Office Action mailed Aug. 8, 2023, in U.S. Appl. No. 16/774,909, 14 pages.

Notice of Allowance mailed Aug. 16, 2023 in U.S. Appl. No. 16/774,841, 8 pages.

(56) References Cited

OTHER PUBLICATIONS

Office Action mailed Sep. 7, 2023 in U.S. Appl. No. 17/151,274, 13 pages.
Office Action mailed Sep. 21, 2023 in U.S. Appl. No. 17/819,099, 24 pages.
D'Allegro, J., Press Release on Nov. 17, 2017, "Soon your car will know when you are having a heart attack—and know how to react," Modern Medicine CNBC accessed at https://www.cnbc.com/2017/11/17/cars-will-know-when-youre-having-a-heart-attack-and-how-to-react.html, accessed on Oct. 10, 2023, 4 pages.
Final Office Action mailed May 16, 2024, in U.S. Appl. No. 16/582,583, 21 pages.
Non-Final Office Action mailed Apr. 15, 2024, in U.S. Appl. No. 16/774,835, 16 pages.
Final Office Action mailed Apr. 9, 2024, in U.S. Appl. No. 16/774,909, 13 pages.
Non-Final Office Action mailed Jun. 18, 2024, in U.S. Appl. No. 18/068,704, 14 pages.
Non-Final Office Action mailed Jul. 15, 2024, in U.S. Appl. No. 18/068,860, 13 pages.
Non-Final Office Action mailed Feb. 29, 2024, in U.S. Appl. No. 18/068,019, 12 pages.
Non-Final Office Action mailed Mar. 5, 2024, in U.S. Appl. No. 18/068,714, 14 pages.
Non-Final Office Action mailed Jan. 31, 2024, in U.S. Appl. No. 18/068,834, 10 pages.
Notice of Allowance mailed Feb. 7, 2024, in U.S. Appl. No. 17/151,274, 8 pages.
Final Office Action mailed on Dec. 24, 2024, in U.S. Appl. No. 16/774,835, filed Jan. 28, 2020, 25 pages.
Final Office Action mailed on Jan. 28, 2025, in U.S. Appl. No. 18/068,077, filed Dec. 19, 2022, 26 pages.
Final Office Action mailed on Oct. 17, 2024, in U.S. Appl. No. 18/068,019, filed Dec. 19, 2022, 17 pages.
Final Office Action mailed on Jan. 24, 2025, in U.S. Appl. No. 18/068,704, filed Dec. 20, 2022, 16 pages.
Final Office Action mailed on Oct. 18, 2024, in U.S. Appl. No. 18/068,714, filed Dec. 20, 2022, 15 pages.
Final Office Action mailed on Oct. 18, 2024, in U.S. Appl. No. 18/068,860, filed Dec. 20, 2022, 15 pages.
Non-Final Office Action mailed on Jul. 30, 2024, in U.S. Appl. No. 18/068,077, filed Dec. 19, 2022, 14 pages.
Non-Final Office Action mailed on Oct. 18, 2024, in U.S. Appl. No. 18/068,834, filed Dec. 20, 2022, 15 pages.
Non-Final Office Action mailed on Jan. 29, 2025, in U.S. Appl. No. 18/068,807, filed Dec. 20, 2022, 25 pages.
Non-Final Office Action mailed on Mar. 5, 2024, in U.S. Appl. No. 17/819,099, filed Aug. 11, 2022, 14 pages.
Notice of Allowance mailed on Sep. 29, 2024, in U.S. Appl. No. 16/774,909, filed Jan. 28, 2020, 10 pages.
Notice of Allowance mailed on Jul. 9, 2024, in U.S. Appl. No. 17/819,099, filed Aug. 11, 2022, 8 pages.
Notice of Allowance mailed on Feb. 9, 2024, in U.S. Appl. No. 16/774,841, filed Jan. 28, 2020, 3 pages.
Pickup, J.C., "Glucose Sensors: Present and Future," International Textbook of Diabetes Mellitus, Third Edition, vol. Two, Defronzo, R.A., eds., pp. 1686-1694, John Wiley & Sons Inc., United States (2004).
English language translation of JP-2014160024-A.
Alva, S., PhD, et al., "Feasibility of Continuous Ketone Monitoring in Subcutaneous Tissue Using a Ketone Sensor," Journal of Diabetes Science and Technology, vol. 15(4), 2021; pp. 768-774.
Del Cano, R., et al., "Ketone Bodies Detection: Wearable and Mobile Sensors for Personalized Medicine an Nutrition," Trends in Analytical Chemistry, vol. 159, 2023, 116938; 11 pages.
English Machine Translation of JP2014160024A, 2014, 22 Pages.
Final Office Action for U.S. Appl. No. 17/138,477, mailed on Apr. 3, 2024, 12 pages.
Final Office Action for U.S. Appl. No. 17/138,477, mailed on Mar. 17, 2023, 12 pages.
Final Office Action for U.S. Appl. No. 17/403,258, mailed on Nov. 13, 2024, 11 pages.
Final Office Action for U.S. Appl. No. 17/818,912, mailed on Oct. 25, 2024, 11 pages.
Final Office Action for U.S. Appl. No. 17/819,038, mailed on Aug. 26, 2024, 10 pages.
Final Office Action mailed Dec. 30, 2020, in U.S. Appl. No. 16/081,162, Ouyang, T., et al., filed Aug. 30, 2018, 12 pages.
Final Office Action mailed Jul. 30, 2024, in U.S. Appl. No. 17/818,143, Ouyang, T., et al., filed Aug. 8, 2022, 11 pages.
Final Office Action mailed Jul. 30, 2024, in U.S. Appl. No. 17/818,770, Ouyang, T., et al., filed Aug. 10, 2022, 13 pages.
International Search Report and Written Opinion for PCT/US2017/020495, mailed on Jul. 10, 2017, 23 pages.
Nakabayashi, Y., et al., "Evaluation of Osmium(II) Complexes as Electron Transfer Mediators Accessible for Amperometric Glucose Sensors," Analytical Sciences 17(8):945-950, Springer, Switzerland (Aug. 2001).
Nikitina, O., et al., "Bi-enzyme Biosensor Based on NAD+- and Glutathione-dependent Recombinant Formaldehyde Dehydrogenase and Diaphorase for Formaldehyde Assay," Sensors and Actuators 125(1):1-9, (Jul. 2007).
Non-Final Office Action for U.S. Appl. No. 17/138,477. mailed on Aug. 21, 2023, 12 pages.
Non-Final Office Action for U.S. Appl. No. 17/138,477, mailed on Sep. 12, 2022, 10 pages.
Non-Final Office Action for U.S. Appl. No. 17/818,143, mailed on Nov. 14, 2024, 12 pages.
Non-Final Office Action for U.S. Appl. No. 17/818,770, mailed on Nov. 5, 2024, 14 pages.
Non-Final Office Action mailed Apr. 26, 2024, in U.S. Appl. No. 17/818,912, Ouyang, T., et al., filed Aug. 10, 2022, 13 pages.
Non-Final Office Action mailed Jan. 24, 2024, in U.S. Appl. No. 17/818,143, Ouyang, T., et al., filed Aug. 8, 2022, 14 pages.
Non-Final Office Action mailed Jan. 31, 2024, in U.S. Appl. No. 17/819,038, Ouyang, T., et al., filed Aug. 11, 2022, 11 pages.
Non-Final Office Action mailed Jul. 22, 2020, in U.S. Appl. No. 16/081,162, Ouyang, T., et al., filed Aug. 30, 2018, 10 pages.
Non-Final Office Action mailed Mar. 12, 2024, in U.S. Appl. No. 17/818,770, Ouyang, T., et al., filed Aug. 10, 2022, 14 pages.
Non-Final Office Action mailed Mar. 25, 2024, in U.S. Appl. No. 17/403,258, Ouyang, T., et al., filed Aug. 16, 2021, 9 pages.
Non-Final Office Action mailed May 7, 2024, in U.S. Appl. No. 17/819,151, Ouyang, T., et al., filed Aug. 11, 2022, 13 pages.
Non-Final Office Action mailed Sep. 16, 2024, in U.S. Appl. No. 18/597,704, Ouyang, T., et al., filed Mar. 6, 2024, 9 pages.
Notice of Allowance for U.S. Appl. No. 17/819,151, mailed on Oct. 22, 2024, 7 pages.
Notice of Allowance mailed Apr. 13, 2021 in U.S. Appl. No. 16/081,162, Ouyang, T., et al., filed Aug. 30, 2018, 7 pages.
Zhang, J., et al., "Continuous Ketone Monitoring: A New Paradigm for Physiologic Monitoring," Journal of Diabetes Science and Technology, vol. 15(4), 2021; pp. 775-780.
Co-pending application, U.S. Appl. No. 19/320,168, filed Sep. 5, 2025.
Co-pending application, U.S. Appl. No. 19/320,172, filed Sep. 5, 2025.
Co-pending application, U.S. Appl. No. 19/320,176, filed Sep. 5, 2025.
Co-pending application, U.S. Appl. No. 19/320,180, filed Sep. 5, 2025.
Co-pending application, U.S. Appl. No. 19/321,772, filed Sep. 8, 2025.
Co-pending application, U.S. Appl. No. 19/321,781, filed Sep. 8, 2025.
Co-pending Application, U.S. Appl. No. 19/340,421, filed Sep. 25, 2025.
Co-pending Application, U.S. Appl. No. 19/340,445, filed Sep. 25, 2025, 118 pages.
Co-pending Application, U.S. Appl. No. 19/340,458, filed Sep. 25, 2025, 119 pages.
Non-Final Office Action for U.S. Appl. No. 19/340,421 mailed on Nov. 28, 2025, 19 pages.

(56) References Cited

OTHER PUBLICATIONS

Non-Final Office Action for U.S. Appl. No. 19/340,445 mailed on Nov. 28, 2025, 20 pages.
Non-Final Office Action for U.S. Appl. No. 19/340,458 mailed on Nov. 28, 2025, 22 pages.
Non-Final Office Action for US Application No. 19/320, 176 mailed on Dec. 3, 2025, 15 pages.
Franco, J.H., et al., "Product Analysis of Operating an Ethanol/O2 Biofuel Cell Shows the Synergy between Enzymes within an Enzymatic Cascade," Journal of The Electrochemical Society 165(9):H575-H579, (2018).
Kowalewska, B., and Kulesza, P.J., "Toward More Efficient Bioelectrocatalytic Oxidation of Ethanol for Amperometric Sensing and Biofuel Cell Technology," Analytical Chemistry 84(21):9564-9571, American Chemical Society, United States (Nov. 2012).
Non-Final Office Action for U.S. Appl. No. 18/068,704 mailed on Dec. 16, 2025; 49 pages.
Non-Final Office Action for U.S. Appl. No. 19/320,168, mailed on Dec. 15, 2025, 8 pages.
Non-Final Office Action for U.S. Appl. No. 19/320,172 mailed on Dec. 4, 2025; 10 pages.
Non-Final Office Action for U.S. Appl. No. 19/320,180 mailed on Dec. 16, 2025; 17 pages.
Notice of Allowance for U.S. Appl. No. 17/818,143 mailed on Oct. 28, 2025; 7 pages.
Notice of Allowance for U.S. Appl. No. 17/818,143 mailed on Jan. 21, 2026; 8 pages.
Notice of Allowance for U.S. Appl. No. 16/744,835 mailed on Jan. 20, 2026; 9 pages.
Notice of Allowance for U.S. Appl. No. 18/068,860 mailed Jan. 22, 2026; 5 pages.
Notice of Allowance for U.S. Appl. No. 18/596,447 mailed on Jan. 21, 2026; 8 pages.

* cited by examiner

ANALYTE SENSORS AND SENSING METHODS FEATURING DUAL DETECTION OF GLUCOSE AND KETONES

CROSS-REFERENCE TO RELATED APPLICATIONS

The present application claims the benefit of priority of U.S. Provisional Application 62/797,566 entitled "Analyte Sensors Employing Multiple Enzymes and Methods Associated Therewith," filed on Jan. 28, 2019, and U.S. Provisional Application 62/884,869 entitled "Analyte Sensors and Sensing Methods Featuring Dual Detection of Glucose and Ketones," filed on Aug. 9, 2019, the entireties of which is incorporated herein by reference.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental conditions. While a single analyte may be singularly dysregulated for a given physiological condition, it is sometimes the case that more than one analyte is concurrently dysregulated, either due to the same physiological condition or resulting from a comorbid (related) physiological condition. When multiple analytes are concurrently dysregulated, the extent of dysregulation may vary for each analyte. As such, each analyte may need to be monitored to obtain a satisfactory evaluation of an individual's health.

Periodic, ex vivo analyte monitoring using a withdrawn bodily fluid can be sufficient to observe a given physiological condition for many individuals. However, ex vivo analyte monitoring may be inconvenient or painful for some persons, particularly if bodily fluid withdrawal needs to occur fairly frequently (e.g., several times per day). Continuous analyte monitoring using an implanted in vivo analyte sensor may be a more desirable approach for individuals having severe analyte dysregulation and/or rapidly fluctuating analyte levels, although it can also be beneficial for other individuals as well due to the convenience offered. Subcutaneous, interstitial, or dermal analyte sensors can provide sufficient measurement accuracy in many cases while affording minimal user discomfort.

Many analytes represent intriguing targets for physiological analyses, provided that a suitable detection chemistry can be identified. To this end, amperometric sensors configured for assaying glucose in vivo have been developed and refined over recent years to aid in monitoring the health of diabetic individuals. Other analytes commonly subject to concurrent dysregulation with glucose in diabetic individuals include, for example, lactate, oxygen, pH, A1c, ketones, and the like. Sensors configured for detecting analytes commonly dysregulated in combination with glucose are known but are considerably less refined at present.

In vivo analyte sensors typically are configured to analyze for a single analyte in order to provide specific analyses, oftentimes employing an enzyme to provide high specificity for a given analyte. Because of such analytical specificity, current in vivo analyte sensors configured for assaying glucose are generally ineffective for assaying other analytes that are frequently dysregulated in combination with glucose or resulting from dysregulated glucose levels. At best, current analyte monitoring approaches require a diabetic individual to wear two different in vivo analyte sensors, one configured for assaying glucose and the other configured for assaying another analyte of interest, such as lactate or ketones. Analyte monitoring approaches employing multiple in vivo analyte sensors may be highly inconvenient for a user. Moreover, when multiple in vivo analyte sensors are used, there is an added cost burden for equipment and an increased statistical likelihood for failure of at least one of the individual in vivo analyte sensors.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
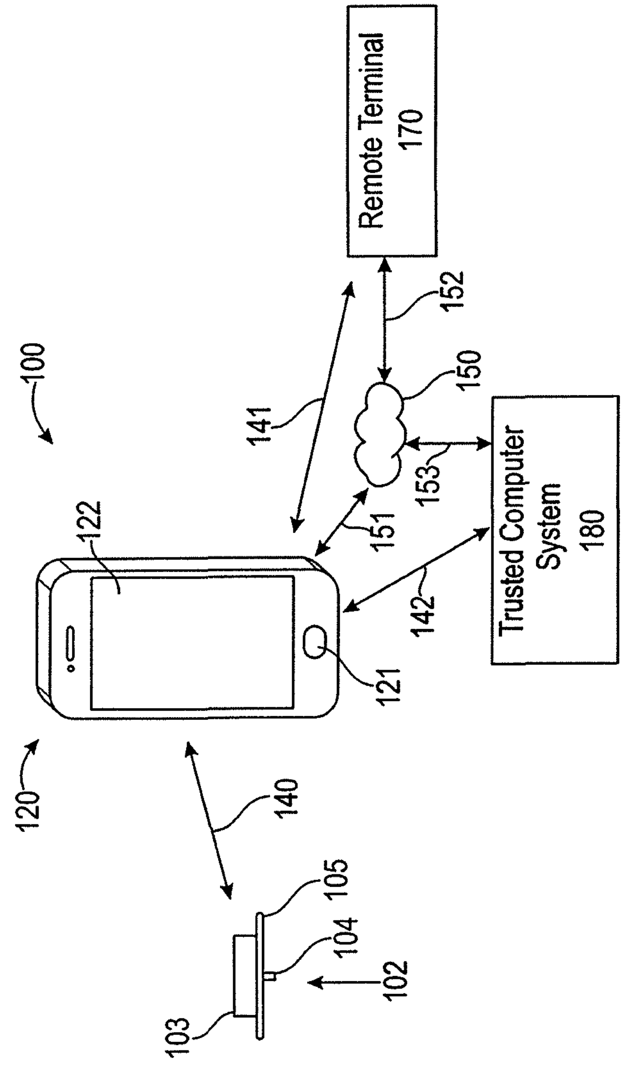
FIG. 1 shows a diagram of an illustrative sensing system that may incorporate an analyte sensor of the present disclosure.

The present disclosure generally describes analyte sensors employing multiple enzymes for detection of two different analytes and, more specifically, analyte sensors employing multiple enzymes for detection of glucose and ketones and corresponding methods for use thereof.

As discussed above, analyte sensors employing an enzyme are commonly used to detect a single analyte, such as glucose or a related analyte, due to the enzyme's frequent specificity for a particular substrate or class of substrate. However, the monitoring of multiple analytes may be complicated by the need to employ a corresponding number of analyte sensors to facilitate the separate detection of each analyte. This approach may be problematic or undesirable, especially when monitoring multiple analytes in vivo, due to issues such as, for example, the cost of multiple analyte sensors, user discomfort when wearing multiple analyte sensors, and an increased statistical likelihood for failure of an individual analyte sensor.

The present disclosure provides analyte sensors that are responsive to both glucose and ketones, two analytes that are commonly dysregulated in diabetic individuals. Since glucose and ketones concentrations may not directly correlate with each other in a diabetic individual also exhibiting ketoacidosis (ketone dysregulation), it may be advantageous to monitor both analytes concurrently using the analyte sensors disclosed herein, potentially leading to improved health outcomes. In addition to providing health benefits for diabetic individuals, the analyte sensors may be beneficial for other individuals who wish to monitor their ketones levels, such as individuals practicing a ketogenic diet. Ketogenic diets may be beneficial for promoting weight loss as well as helping epileptic individuals manage their condition. Concurrent glucose monitoring during ketogenic diet monitoring may offer related advantages.

In particular, the present disclosure provides analyte sensors in which a glucose-responsive active area and a ketones-responsive active area are present within the tail of a single analyte sensor, thereby allowing both analytes to be monitored concurrently for identifying potential dysregulation thereof using the single analyte sensor. As evident from the description above, the concurrent detection of glucose and ketones using a single analyte sensor may provide several advantages over monitoring approaches employing separate analyte sensors. Various physical dispositions of the glucose-responsive active area and the ketones-responsive active area are possible within the analyte sensors, as discussed hereinafter. Particular implementations of the present disclosure include sensor architectures in which the glucose-responsive active area and the ketones-responsive active area may be interrogated separately to determine the concentration of each analyte, such as through disposing the active areas upon separate working electrodes. As discussed hereinafter, there are challenges associated with incorporating active areas featuring different detection chemistries upon a single analyte sensor, which are addressed by the present disclosure.

Glucose-responsive analyte sensors are a well-studied and still developing field to aid diabetic individuals in better managing their health. Despite the prevalence of comorbid analyte dysregulation in diabetic individuals, sensor chemistries suitable for detecting ketones and other analytes commonly dysregulated in combination with glucose have significantly lagged behind the more well-developed glucose detection chemistries. The present disclosure alleviates this deficiency by providing sensor chemistries suitable for detecting ketones with good response stability over a range of ketones concentrations, particularly detection chemistries utilizing enzyme systems comprising at least two enzymes that are capable of acting in concert to facilitate detection of ketones. As used herein, the term "in concert" refers to a coupled enzymatic reaction, in which the product of a first enzymatic reaction becomes the substrate for a second enzymatic reaction, and the second enzymatic reaction serves as the basis for measuring the concentration of the substrate (analyte) reacted during the first enzymatic reaction. Although defined in terms of two coupled enzymatic reactions, it is to be appreciated that more than two enzymatic reactions may be coupled as well in some instances. For example, the product of a first enzymatic reaction may become the substrate of a second enzymatic reaction, and the product of the second enzymatic reaction may become the substrate for a third enzymatic reaction, with the third enzymatic reaction serving as the basis for measuring the concentration of the substrate (analyte) reacted during the first enzymatic reaction. Discussion of suitable enzyme systems for detecting ketones according to the disclosure herein follows hereinbelow.

It may be desirable to utilize two or more enzymes acting in concert with one another to detect a given analyte of interest when a single enzyme is unable to facilitate detection. Situations in which a single enzyme may be ineffective for promoting analyte detection include, for example, those in which the enzyme is inhibited by one or more products of the enzymatic reaction or is unable to cycle between an oxidized state and reduced state when disposed within an analyte sensor. Some products produced by a single enzyme may not be electrochemically detectable.

Even having suitable detection chemistries in hand, combining a glucose-responsive active area and a ketones-responsive active area upon a single analyte sensor is not a straightforward matter. Glucose-responsive analyte sensors commonly employ a membrane overcoating the glucose-responsive active area to function as a mass transport limiting membrane and/or to improve biocompatibility. Limiting glucose access to the glucose-responsive active area with a mass transport limiting membrane can aid in avoiding sensor overload (saturation), thereby improving detection performance and accuracy. A mass transport limiting membrane may act as a diffusion-limiting barrier to reduce the rate of mass transport of glucose to accomplish the foregoing. The mass transport limiting membrane may be homogeneous and comprise a single membrane polymer in conventional glucose-responsive sensors. Unfortunately, glucose and ketones exhibit significantly different permeability values through a given membrane material, such that if a single mass transport limiting membrane overcoats the active areas of an analyte sensor capable of detecting both glucose and ketones, significantly different sensitivities may be realized for each analyte, thereby complicating one's ability to detect glucose and ketones concurrently and accurately. Although analyte sensitivity issues may be addressed, in principle, by adjusting the membrane thickness and/or altering the size of the active areas with respect to one another, these solutions may be difficult to implement in practice.

In response to the foregoing, the present disclosure also provides membrane compositions and methods for deposition thereof that are suitable to facilitate concurrent detection of glucose and ketones. Specifically, the present disclosure provides membrane compositions having different permeability values that may be disposed separately as distinct compositions upon the glucose-responsive active area and the ketones-responsive active area. Surprisingly, a membrane polymer suitable for use as a mass transport limiting membrane in a glucose-responsive analyte sensor may also be suitably incorporated in a multi-component mass transport limiting membrane for overcoating the active area in a ketones-responsive analyte sensor, even when the membrane polymer alone is otherwise unsuitable for use with ketones due to poor performance (e.g., undesired permeability values). Advantageously, the architectures of the analyte sensors disclosed herein allow a continuous membrane having a homogenous membrane portion to be disposed upon the glucose-responsive active area of the analyte sensors and a multi-component membrane portion to be disposed upon the ketones-responsive active area of the analyte sensors, thereby levelizing the permeabilities of each analyte concurrently to afford improved sensitivity and detection accuracy. As used herein, the term "homogenous membrane" refers to a membrane comprising a single type of membrane polymer, and the term "multi-component membrane" refers to a membrane comprising two or more types of membrane polymers. Both bilayer and admixed membranes may be suitable for use as the multi-component membrane in the disclosure herein. By utilizing a multi-component membrane in conjunction with the sensor architectures disclosed herein, manufacturing advantages may be realized when combining glucose-responsive and ketones-responsive detection chemistries with one another, as compared to manufacturing approaches that alter the membrane thickness and/or the size of the active areas for adjusting the sensitivity of one of the analytes.

Before describing the analyte sensors of the present disclosure in further detail, a brief overview of suitable in vivo analyte sensor configurations and sensor systems employing the analyte sensors will be provided first so that the embodiments of the present disclosure may be better understood. FIG. 1 shows a diagram of an illustrative sensing system that may incorporate an analyte sensor of the present disclosure, specifically an analyte sensor comprising a glucose-responsive active area and a ketones-responsive active area. As shown, sensing system 100 includes sensor control device 102 and reader device 120 that are configured to communicate with one another over a local communication path or link, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer system 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety. Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode and a glucose-responsive active area and a ketones-responsive active area upon a surface of the at least one working electrode to facilitate detection of these analytes. A counter electrode may be present in combination with the at least one working electrode. Particular electrode configurations upon the sensor tail are described in more detail below in reference to FIGS. 3A-5D.

One or more mass transport limiting membranes may overcoat the glucose-responsive active area and the ketones-responsive active area upon the at least one working electrode, as also described in further detail below. The glucose-responsive active area may comprise a glucose-responsive enzyme and the ketones-responsive active area may comprise an enzyme system comprising at least two enzymes that are capable of acting in concert to facilitate detection of ketones. Suitable enzyme systems are further described below in reference to FIGS. 2A-2C. The glucose-responsive active area and the ketones-responsive active area may each include a polymer to which at least some of the enzymes are covalently bonded, according to various embodiments. In various embodiments of the present disclosure, glucose and ketones may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine concentrations of glucose and/or ketones in vivo.

Referring still to FIG. 1, sensor 104 may automatically forward data to reader device 120. For example, analyte concentration data (i.e., glucose and/or ketones concentrations) may be communicated automatically and periodically, such as at a certain frequency as data is obtained or after a certain time period has passed, with the data being stored in a memory until transmittal (e.g., every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a user does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle is subsequently withdrawn after facilitating sensor insertion.

Figure 2A:
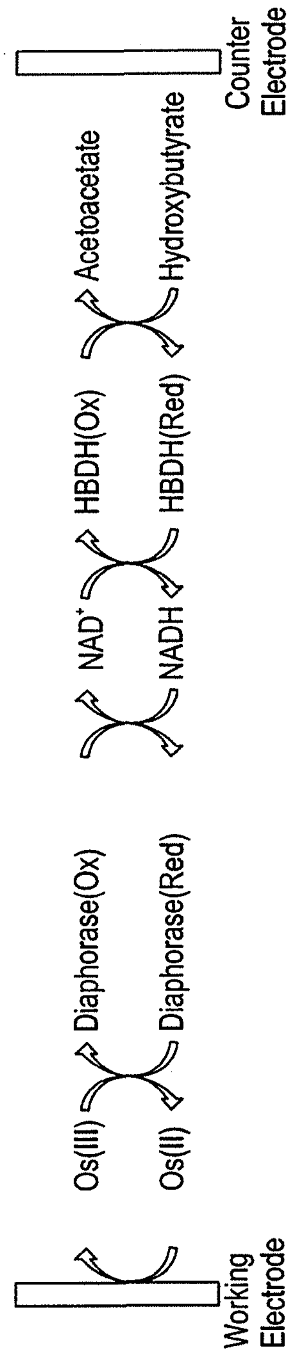
FIGS. 2A-2C show diagrams of particular enzyme systems that may be used for detecting ketones according to the disclosure herein.
Figure 2B:
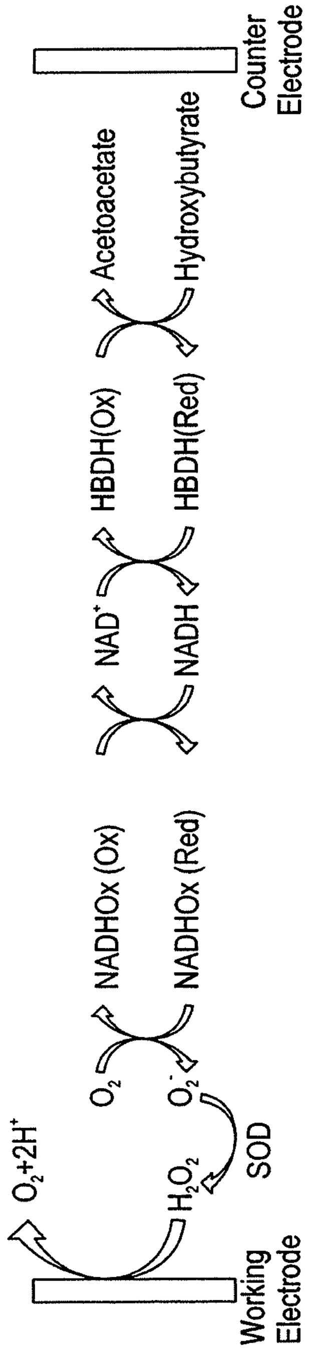
Figure 2C:
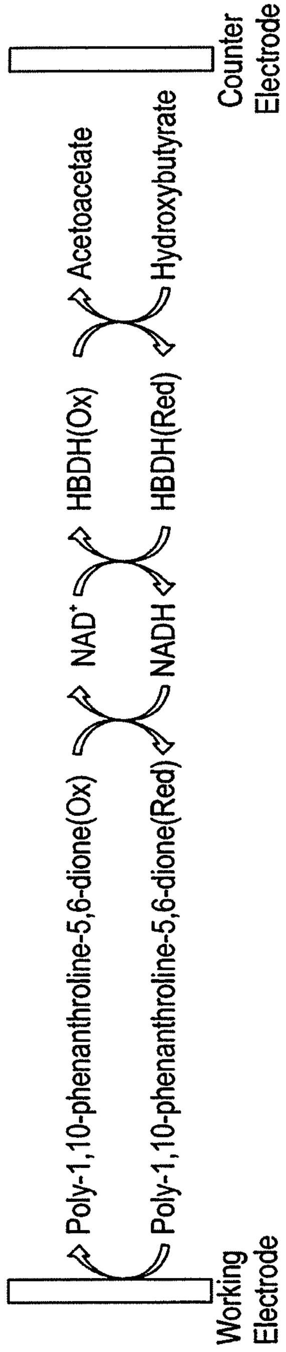

Referring now to FIGS. 2A-2C, particular enzyme systems that may be used for detecting ketones according to the disclosure herein will be described in further detail. In the depicted enzymatic reactions, β-hydroxybutyrate serves as a surrogate for ketones formed in vivo. As shown in FIG. 2A, one pair of concerted enzymes that may be used for detecting ketones according to the disclosure herein is β-hydroxybutyrate dehydrogenase (HBDH) and diaphorase, which may be deposited within a ketones-responsive active area upon the surface of at least one working electrode, as described further herein. When a ketones-responsive active area contains this pair of concerted enzymes, β-hydroxybutyrate dehydrogenase may convert β-hydroxybutyrate and oxidized nicotinamide adenine dinucleotide ($NAD^+$) into acetoacetate and reduced nicotinamide adenine dinucleotide (NADH), respectively. The enzyme cofactors $NAD^+$ and NADH aid in promoting the concerted enzymatic reactions disclosed herein. The NADH may then undergo oxidation under diaphorase mediation, with the electrons transferred during this process providing the basis for ketone detection at the working electrode. Thus, there is a 1:1 molar correspondence between the amount of electrons transferred to the working electrode and the amount of p-hydroxybutyrate converted, thereby providing the basis for ketones detection and quantification based upon the measured amount of current at the working electrode. Transfer of the electrons resulting from NADH oxidation to the working electrode may take place through an electron transfer agent, such as an osmium (Os) compound, as described further below. Albumin may be present as a stabilizer with this pair of concerted enzymes. According to particular embodiments, the β-hydroxybutyrate dehydrogenase and the diaphorase may be covalently bonded to a polymer within the ketones-responsive active area of the analyte sensors. The $NAD^+$ may or may not be covalently bonded to the polymer, but if the $NAD^+$ is not covalently bonded, it may be physically retained within the ketones-responsive active area. A membrane overcoating the ketones-responsive active area may aid in retaining the NAD within the ketones-responsive active area while still permitting sufficient inward diffusion of ketones to permit detection thereof. Suitable membrane polymers for overcoating the ketones-responsive active area are discussed further herein.

Other suitable chemistries for enzymatically detecting ketones are shown in FIGS. 2B and 2C. In both instances, there is again a 1:1 molar correspondence between the amount of electrons transferred to the working electrode and the amount of β-hydroxybutyrate converted, thereby providing the basis for ketones detection.

As shown in FIG. 2B, β-hydroxybutyrate dehydrogenase (HBDH) may again convert β-hydroxybutyrate and $NAD^+$ into acetoacetate and NADH, respectively. Instead of electron transfer to the working electrode being completed by diaphorase (see FIG. 2A) and a transition metal electron transfer agent, the reduced form of NADH oxidase (NADHOx (Red)) undergoes a reaction to form the corresponding oxidized form (NADHOx (Ox)). NADHOx (Red) may then reform through a reaction with molecular oxygen to produce superoxide, which may undergo subsequent conversion to hydrogen peroxide under superoxide dismutase (SOD) mediation. The hydrogen peroxide may then undergo oxidation at the working electrode to provide a signal that may be correlated to the amount of ketones that were initially present. The SOD may be covalently bonded to a polymer in the ketones-responsive active area, according to various embodiments. Like the enzyme system shown in FIG. 2A, the β-hydroxybutyrate dehydrogenase and the NADH oxidase may be covalently bonded to a polymer in the ketones-responsive active area, and the $NAD^+$ may or may not be covalently bonded to a polymer in the ketones-responsive active area. If the $NAD^+$ is not covalently bonded, it may be physically retained within the ketones-responsive active area, with a membrane polymer promoting retention of the $NAD^+$ within the ketones-responsive active area.

As shown in FIG. 2C, another enzymatic detection chemistry for ketones may utilize β-hydroxybutyrate dehydrogenase (HBDH) to convert β-hydroxybutyrate and $NAD^+$ into acetoacetate and NADH, respectively. The electron transfer cycle in this case is completed by oxidation of poly-1,10-phenanthroline-5,6-dione at the working electrode to reform NAD. The poly-1,10-phenanthroline-5,6-dione may or may not be covalently bonded to a polymer within the ketones-responsive active area. Like the enzyme system shown in FIG. 2A, the β-hydroxybutyrate dehydrogenase may be covalently bonded to a polymer in the ketones-responsive active area, and the NAD may or may not be covalently bonded to a polymer in the ketones-responsive active area. Inclusion of an albumin in the active area may provide a surprising improvement in response stability. A suitable membrane polymer may promote retention of the $NAD^+$ within the ketones-responsive active area.

The glucose-responsive active areas in the analyte sensors disclosed herein may be physically adsorbed to a working electrode surface and may comprise a glucose-responsive enzyme, such as glucose oxidase or glucose dehydrogenase. The glucose-responsive active area may comprise a polymer that is covalently bound to the glucose-responsive enzyme, according to various embodiments. Suitable polymers for inclusion in the active areas are described below.

The analyte sensors disclosed herein may feature active areas of different types (i.e., a glucose-responsive active area and a ketones-responsive active area) upon a single working electrode or upon two or more separate working electrodes. Single working electrode sensor configurations may employ two-electrode or three-electrode detection motifs, according to various embodiments of the present disclosure and as described further herein. Sensor configurations featuring a single working electrode are described hereinafter in reference to FIGS. 3A-3C. Each of these sensor configurations may suitably incorporate a glucose-responsive active area and a ketones-responsive active area according to various embodiments of the present disclosure. Sensor configurations featuring multiple working electrodes are described thereafter in reference to FIGS. 4 and 5A-5D. When multiple working electrodes are present, a ketones-responsive active area may be disposed upon a first working electrode and a glucose-responsive active area may be disposed upon a second working electrode. Sensor configurations employing multiple working electrodes may be particularly advantageous for incorporating both a glucose-responsive active area and a ketones-responsive active area according to the disclosure herein, since mass transport limiting membranes having differing compositions and/or different permeability values may be deposited more readily during manufacturing when the active areas are separated and/or spaced apart in this manner. Particular sensor configurations featuring multiple working electrodes disposed in a manner to facilitate deposition of mass transport limiting membranes having differing compositions, particularly by dip coating, upon each working electrode are shown in FIGS. 5A-5D. Suitable techniques for depositing the mass transport limiting membranes disclosed herein include, for example, spray coating, painting, inkjet printing, stenciling, roller coating, dip coating, or the like, and any combination thereof.

When a single working electrode is present in an analyte sensor, three-electrode sensor configurations may comprise a working electrode, a counter electrode, and a reference electrode. Related two-electrode sensor configurations may comprise a working electrode and a second electrode, in which the second electrode may function as both a counter electrode and a reference electrode (i.e., a counter/reference electrode). In both two-electrode and three-electrode sensor configurations, both the glucose-responsive active area and the ketones-responsive active area may be disposed upon the single working electrode. In some embodiments, the various electrodes may be at least partially stacked (layered) upon one another and/or laterally spaced apart from one another upon the sensor tail. Suitable sensor configurations may be substantially flat in shape or substantially cylindrical in shape, with the glucose-responsive active area and the ketones-responsive active area being laterally spaced apart upon the working electrode. In all of the sensor configurations disclosed herein, the various electrodes may be electrically isolated from one another by a dielectric material or similar insulator.

Analyte sensors featuring multiple working electrodes may similarly comprise at least one additional electrode. When one additional electrode is present, the one additional electrode may function as a counter/reference electrode for each of the multiple working electrodes. When two additional electrodes are present, one of the additional electrodes may function as a counter electrode for each of the multiple working electrodes and the other of the additional electrodes may function as a reference electrode for each of the multiple working electrodes.

Figure 3A:
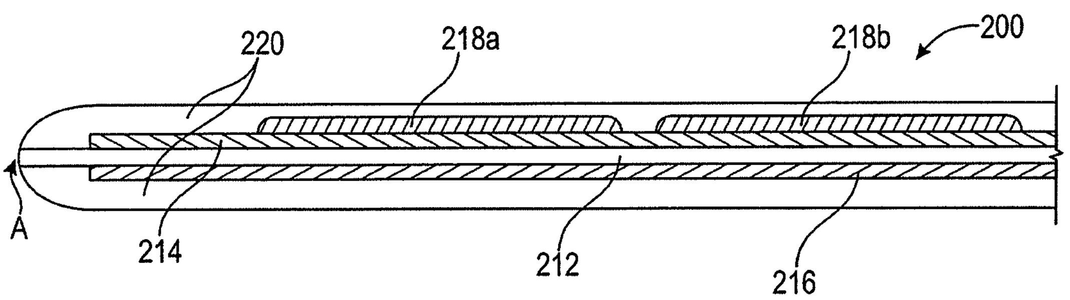
FIGS. 3A-3C show cross-sectional diagrams of analyte sensors having a glucose-responsive active area and a ketones-responsive active area upon a single working electrode.

Analyte sensor configurations having a single working electrode will now be described in further detail. FIG. 3A shows a cross-sectional diagram of an illustrative two-electrode analyte sensor configuration having a single working electrode, which is compatible for use in some embodiments of the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active areas 218*a* and 218*b* (i.e., a glucose-responsive active area and a ketones-responsive active area) are laterally spaced apart from one another upon the surface of working electrode 214. In the various sensor configurations shown herein, active areas 218*a* and 218*b* may comprise multiple spots or a single spot configured for detection of each analyte. Analyte sensor 200 may be operable for assaying glucose and ketones by any of coulometric, amperometric, voltammetric, or potentiometric electrochemical detection techniques.

Referring still to FIG. 3A, membrane 220 overcoats at least active areas 218*a* and 218*b* and may optionally overcoat some or all of working electrode 214 and/or counter/reference electrode 216, or the entirety of analyte sensor 200. One or both faces of analyte sensor 200 may be overcoated with membrane 220. Membrane 220 may comprise one or more polymeric membrane materials (membrane polymers) having suitable capabilities for limiting analyte flux to active areas 218*a* and 218*b*. Although not readily apparent in FIG. 3A, the composition of membrane 220 may vary at active areas 218*a* and 218*b* in order to differentially regulate the analyte flux at each location, as described further herein. For example, membrane 220 may be sprayed and/or printed onto active areas 218*a* and 218*b*, such that the composition of membrane 220 differs at each location. In another alternative, membrane 220 may be deposited by dip coating starting from end A of analyte sensor 200. Specifically, end A of analyte sensor 200 may be dipped in a first coating formulation to overcoat active area 218*a*. After partially curing the first coating formulation upon active area 218*a*, end A of analyte sensor 200 may be dipped in a second coating formulation to overcoat both active areas 218*a* and 218*b* with the second coating formulation. As such, membrane 220 may be continuous and feature a bilayer at active area 218*a* and be homogeneous at active area 218*b*.

Figure 3B:
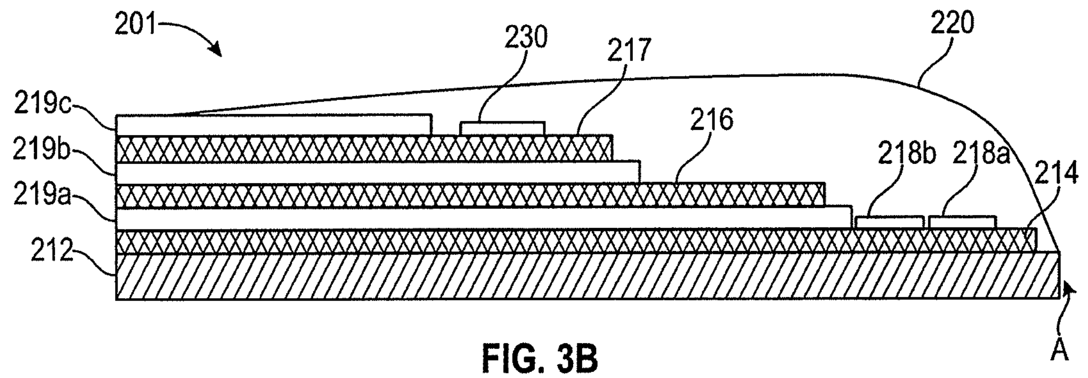
Figure 3C:
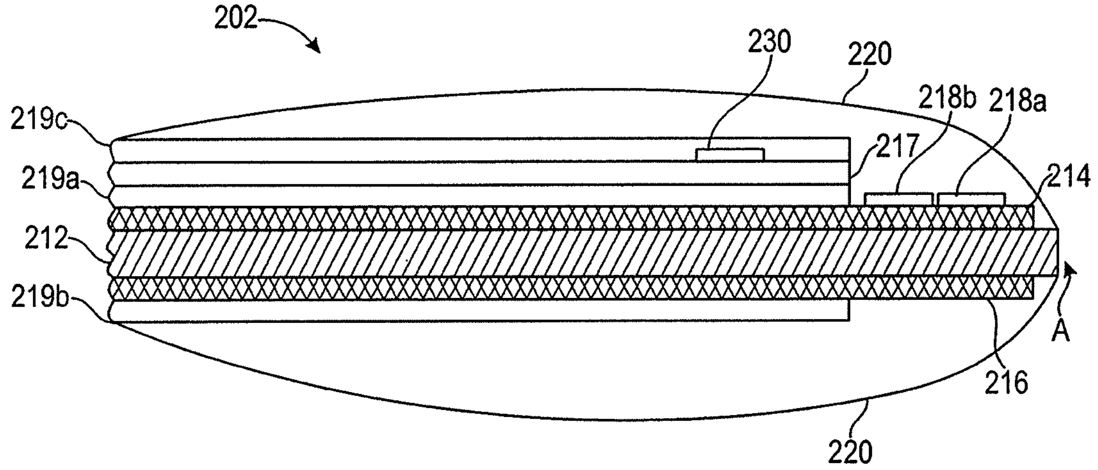

FIGS. 3B and 3C show cross-sectional diagrams of illustrative three-electrode sensor configurations having a single working electrode, which are compatible for use in some embodiments of the disclosure herein. Three-electrode sensor configurations featuring a single working electrode may be similar to that shown for analyte sensor 200 in FIG. 3A, except for the inclusion of additional electrode 217 in analyte sensors 201 and 202 (FIGS. 3B and 3C). With additional electrode 217, electrode 216 may then function as either a counter electrode or a reference electrode, and additional electrode 217 may fulfill the other electrode function not otherwise accounted for. Working electrode 214 continues to fulfill its original function in either case. Additional electrode 217 may be disposed upon either working electrode 214 or electrode 216, with a separating layer of dielectric material in between each. For example, as depicted in FIG. 3B, electrodes 214, 216 and 217 are located upon the same face of substrate 212 and are electrically isolated from one another by dielectric layers 219*a*, 219*b* and 219*c* in between. Alternately, at least one of electrodes 214, 216 and 217 may be located upon opposite faces of substrate 212, as shown in FIG. 3C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 3B and 3C. As with analyte sensor 200 shown in FIG. 3A, active areas 218*a* and 218*b* in analyte sensors 201 and 202 are disposed laterally spaced apart from one another upon working electrode 214 in the sensor configurations of FIGS. 3B and 3C. Like analyte sensor 200, analyte sensors 201 and 202 may be operable for assaying glucose and ketones by any of coulometric, amperometric, voltammetric, or potentiometric electrochemical detection techniques.

Also like analyte sensor 200, membrane 220 may also overcoat active areas 218*a* and 218*b*, as well as other sensor components, in analyte sensors 201 and 202. Additional electrode 217 may be overcoated with membrane 220 in some embodiments. Although FIGS. 3B and 3C have depicted all of electrodes 214, 216 and 217 as being overcoated with membrane 220, it is to be recognized that only working electrode 214 or active areas 218*a* and 218*b* may be overcoated in some embodiments. Although not apparent in FIGS. 3B and 3C, the thickness of membrane 220 may be the same or different at various locations, such as varying thicknesses at active areas 218*a* and 218*b*. Likewise, membrane 220 may also vary compositionally at active areas 218*a* and 218*b* in order to differentially regulate the analyte flux at each location. For example, dip coating from end A of analyte sensors 201 and 202 may be used to deposit a continuous membrane featuring a bilayer membrane portion at active area 218*a* and a homogeneous membrane portion at active area 218*b*, as described in more detail above for FIG. 3A. As in two-electrode analyte sensor configurations (FIG. 3A), one or both faces of analyte sensors 201 and 202 may be overcoated with membrane 220 in the sensor configurations of FIGS. 3B and 3C, or the entirety of analyte sensors 201 and 202 may be overcoated. Accordingly, the three-electrode sensor configurations shown in FIGS. 3B and 3C should be understood as being illustrative and non-limiting of the disclosure herein, with alternative electrode and/or layer configurations residing within the scope of the present disclosure.

Sensor configurations having multiple working electrodes, specifically two working electrodes, will now be described in further detail in reference to FIGS. 4 and 5A-5D. Although the following description is primarily directed to sensor configurations having two working electrodes, it is to be appreciated that more than two working electrodes may be incorporated through extension of the disclosure herein. Additional working electrodes may be used to impart additional sensing capabilities to the analyte sensors beyond just glucose and ketones sensing.

Figure 4:
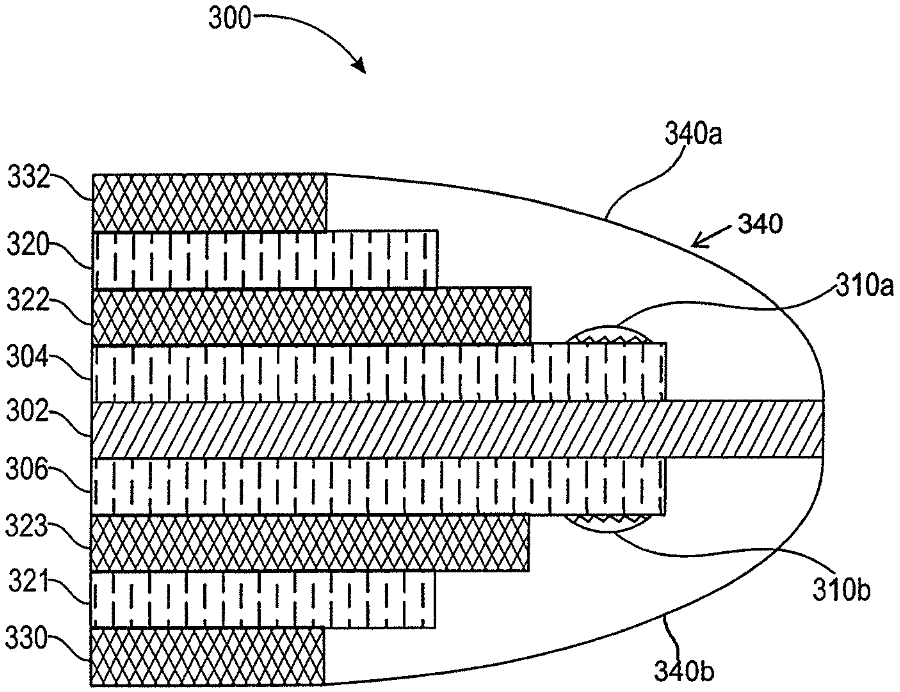
FIG. 4 shows a cross-section diagram of an analyte sensor having a glucose-responsive active area and a ketones-responsive active area upon separate working electrodes.

FIG. 4 shows a cross-sectional diagram of an illustrative analyte sensor configuration having two working electrodes, a reference electrode and a counter electrode, which is compatible for use in some embodiments of the disclosure herein. As shown in FIG. 4, analyte sensor 300 includes working electrodes 304 and 306 disposed upon opposite faces of substrate 302. Active area 310*a* is disposed upon the surface of working electrode 304, and active area 310*b* is disposed upon the surface of working electrode 306. Active areas 310*a* and 310*b* may be glucose-responsive and ketones-responsive, according to various embodiments of the present disclosure. Counter electrode 320 is electrically isolated from working electrode 304 by dielectric layer 322, and reference electrode 321 is electrically isolated from working electrode 306 by dielectric layer 323. Outer dielectric layers 330 and 332 are positioned upon reference electrode 321 and counter electrode 320, respectively. Membrane 340 has first membrane portion 340*a* and second membrane portion 340*b*, which separately overcoat at least active areas 310*a* and 310*b*, respectively, according to various embodiments, with other components of analyte sensor 300 or the entirety of analyte sensor 300 optionally being overcoated with first membrane portion 340*a* and/or second membrane portion 340*b* as well. Again, membrane 340 may be continuous but vary compositionally within first membrane portion 340*a* and second membrane portion 340*b* (i.e., upon active areas 310*a* and 310*b*) in order to afford different permeability values for differentially regulating the analyte flux at each location. For example, different membrane formulations may be sprayed and/or printed onto the opposing faces of analyte sensor 300. Dip coating techniques may also be appropriate, particularly for depositing at least a portion of a bilayer membrane upon one of active areas 310*a* and 310*b*. Accordingly, one of first membrane portion 340*a* and second membrane portion 340*b* may comprise a bilayer membrane and the other of first membrane portion 340*a* and second membrane portion 340*b* may comprise a single membrane polymer, according to particular embodiments of the present disclosure. Like analyte sensors 200, 201 and 202, analyte sensor 300 may be operable for assaying glucose and ketones by any of coulometric, amperometric, voltammetric, or potentiometric electrochemical detection techniques.

Alternative sensor configurations having multiple working electrodes and differing from that shown in FIG. 4 may feature a counter/reference electrode instead of separate counter and reference electrodes 320,321, and/or feature layer and/or membrane arrangements varying from those expressly depicted. For example, the positioning of counter electrode 320 and reference electrode 321 may be reversed from that depicted in FIG. 4. In addition, working electrodes 304 and 306 need not necessarily reside upon opposing faces of substrate 302 in the manner shown in FIG. 4.

Although suitable sensor configurations may feature electrodes that are substantially planar in character, it is to be appreciated that sensor configurations featuring non-planar electrodes may be advantageous and particularly suitable for use in the disclosure herein. In particular, substantially cylindrical electrodes that are disposed concentrically with one another may facilitate deposition of a mass transport limiting membrane, as described hereinbelow. FIGS. 5A-5D show perspective views of analyte sensors featuring substantially cylindrical electrodes that are disposed concentrically with respect to one another. Although FIGS. 5A-5D have depicted sensor configurations featuring two working electrodes, it is to be appreciated that similar sensor configurations having either one working electrode or more than two working electrodes are possible through extension of the disclosure herein.

Figure 5A:
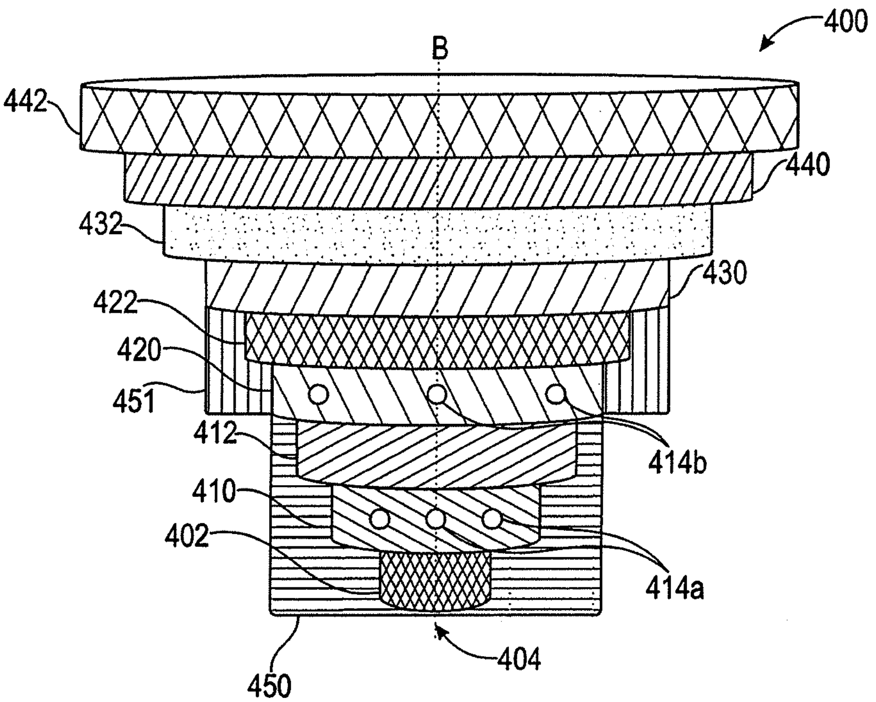
FIGS. 5A-5D show perspective views of analyte sensors featuring substantially cylindrical electrodes that are disposed concentrically with respect to one another.

FIG. 5A shows a perspective view of an illustrative sensor configuration in which multiple electrodes are substantially cylindrical and are disposed concentrically with respect to one another about a central substrate. As shown, analyte sensor 400 includes central substrate 402 about which all electrodes and dielectric layers are disposed concentrically with respect to one another. In particular, working electrode 410 is disposed upon the surface of central substrate 402, and dielectric layer 412 is disposed upon a portion of working electrode 410 distal to sensor tip 404. Working electrode 420 is disposed upon dielectric layer 412, and dielectric layer 422 is disposed upon a portion of working electrode 420 distal to sensor tip 404. Counter electrode 430 is disposed upon dielectric layer 422, and dielectric layer 432 is disposed upon a portion of counter electrode 430 distal to sensor tip 404. Reference electrode 440 is disposed upon dielectric layer 432, and dielectric layer 442 is disposed upon a portion of reference electrode 440 distal to sensor tip 404. As such, exposed surfaces of working electrode 410, working electrode 420, counter electrode 430, and reference electrode 440 are spaced apart from one another along longitudinal axis B of analyte sensor 400. Spacing apart of working electrode 410 and working electrode 420 along a longitudinal axis may also be realized in substantially planar sensor configurations as well, such as those provided above.

Referring still to FIG. 5A, active areas **414*a* and 414*b* are disposed upon the exposed surfaces of working electrodes 410 and 420, respectively, thereby allowing contact with a fluid to take place for sensing of glucose and/or ketones to take place. Although active areas 414*a* and 414*b* have been depicted as three discrete spots in FIG. 5A, it is to be appreciated that fewer or greater than three spots may be present in alternative sensor configurations. Each of active areas 414*a* and 414*b* can also be a continuous layer that is disposed as a ring upon the exposed surface of working electrodes 410 and 420**, respectively.

Similar to the sensor configuration discussed above, at least working electrodes 410 and 420 and active areas **414*a* and 414*b* thereon are overcoated with a membrane in the sensor configuration of FIG. 5A. Although a membrane featuring a single composition may overcoat active areas 414*a* and 414*b*, the membrane compositions may differ compositionally in each location in order to afford different permeability values, thereby levelizing the sensor response for each analyte. In the sensor configuration depicted in FIG. 5A, membrane portion 450 having a first composition overcoats working electrode 410 and active area 414*a*, along with optional overcoating of dielectric layer 412, and membrane portion 451 having a second composition differing from the first composition overcoats working electrode 420 and active area 414*b*, along with optional overcoating of dielectric layer 412 and/or dielectric layer 422. Although not shown in FIG. 5A, counter electrode 430, reference electrode 440, and dielectric layers 432 and 442 may also be overcoated with membrane 451**.

Figure 5B:
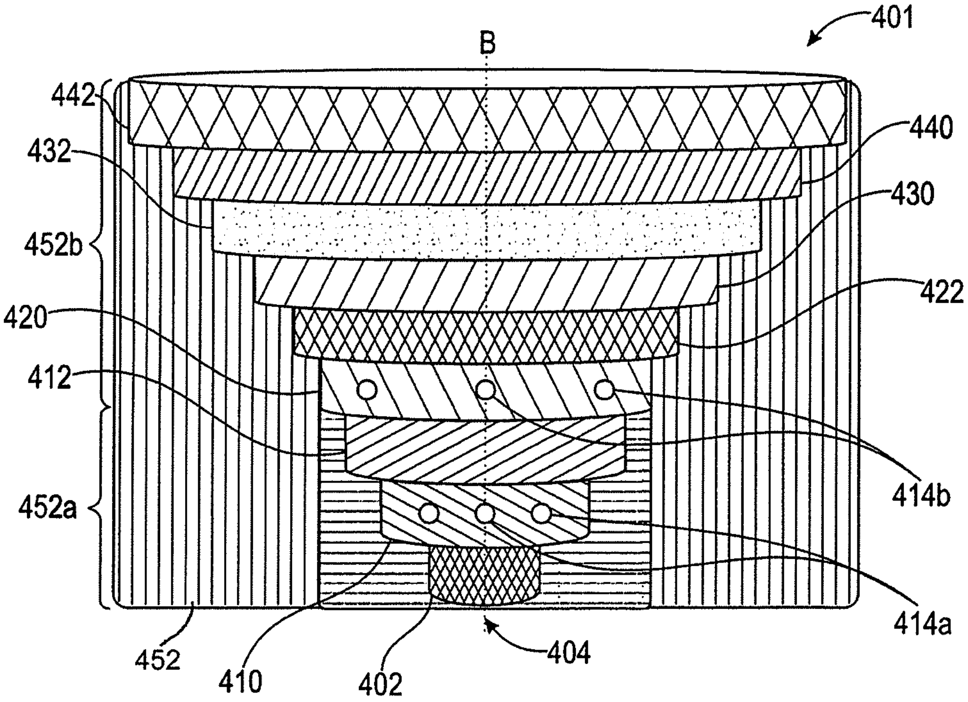

FIG. 5B shows an alternative sensor configuration to that depicted in FIG. 5A, in which all components upon the sensor tail are membrane-coated. In the sensor configuration shown in FIG. 5B, sensor 401 contains working electrode 410, active area **414*a*, and dielectric layer 412 that are each overcoated with first portion 452*a* of membrane 452. First portion 452*a* comprises two membrane layers, thereby defining a bilayer membrane. Second portion 452*b* of membrane 452 overcoats working electrode 420, active area 414*b*, and the remainder of the sensor tail (i.e., counter electrode 430, reference electrode 440, and dielectric layers 422, 432 and 442) with a single membrane polymer. While shown as having two portions 452*a* and 452*b*, it is to be appreciated that additional portions may be present. Moreover, first portion 452*a* may be a bilayer membrane, as depicted, or a homogenous admixture of multiple membrane polymers. Sensor configurations having first portion 452*a* as a bilayer membrane may feature an active area 414*a* that is ketones-responsive and an active area 414*b* that is glucose-responsive, according to various embodiments of the present disclosure. Further details regarding suitable membrane polymers and techniques for deposition of first and second portions 452*a*,452*b* of membrane 452** at each location are provided hereinbelow.

Figure 5C:
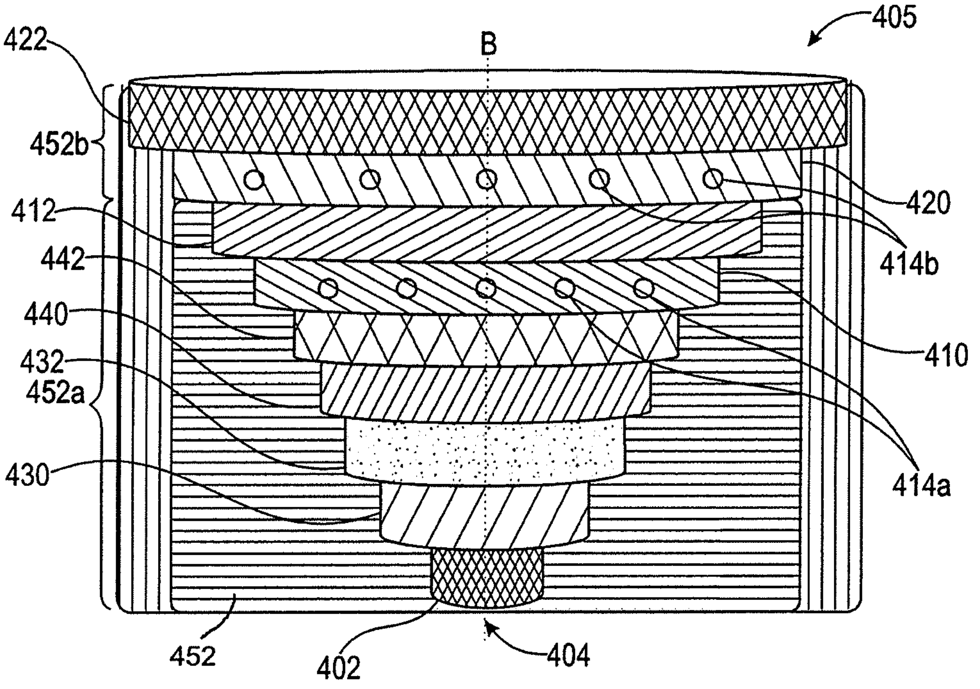

It is to be further appreciated that the positioning of the various electrodes in FIGS. 5A and 5B may differ from that expressly depicted. For example, the positions of counter electrode 430 and reference electrode 440 may be reversed from the depicted configurations in FIGS. 5A and 5B. Similarly, the positions of working electrodes 410 and 420 are not limited to those that are expressly depicted in FIGS. 5A and 5B. FIG. 5C shows an alternative sensor configuration to that shown in FIG. 5B, in which sensor 405 contains counter electrode 430 and reference electrode 440 that are located more proximal to sensor tip 404 and working electrodes 410 and 420 that are located more distal to sensor tip 404. Sensor configurations in which working electrodes 410 and 420 are located more distal to sensor tip 404 may be advantageous by providing a larger surface area for deposition of active areas **414*a* and 414*b* (five discrete sensing spots illustratively shown in FIG. 5C), thereby facilitating an increased signal strength in some cases. The locations of the bilayer membrane defined by first portion 452*a* and the homogeneous membrane defined by second portion 452*b* have been similarly adjusted to accommodate the change in location of working electrodes 410 and 420**.

Figure 5D:
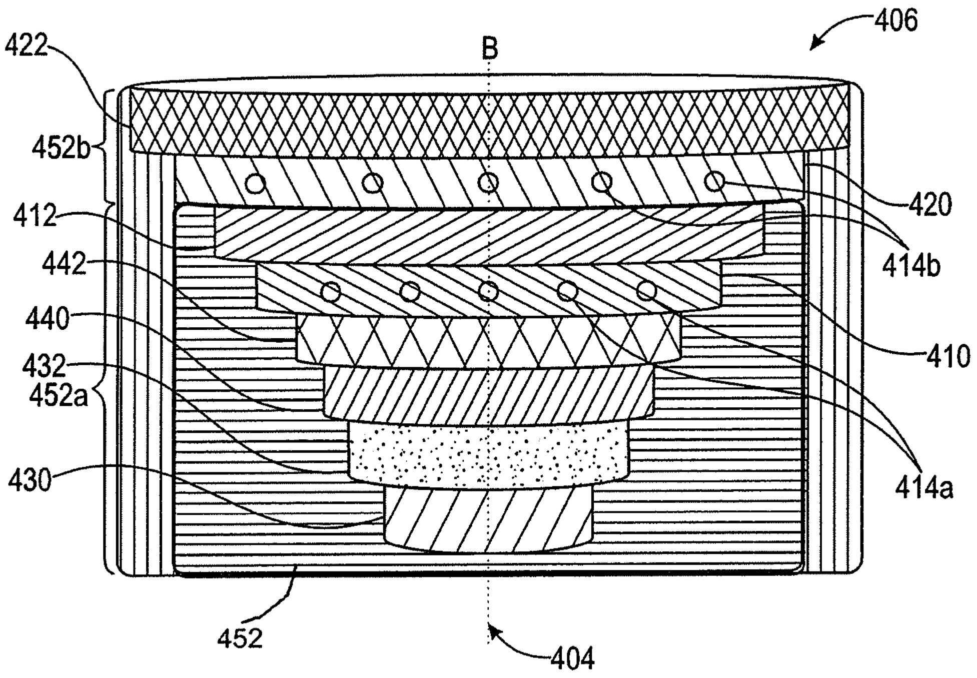

Although FIGS. 5A-5C have depicted sensor configurations that are each supported upon central substrate 402, it is to be appreciated that alternative sensor configurations may be electrode-supported instead and lack central substrate 402. In particular, the innermost concentric electrode may be utilized to support the other electrodes and dielectric layers. FIG. 5D shows an alternative sensor configuration to that depicted in FIG. 5C, in which sensor 406 does not contain central substrate 402 and counter electrode 430 is the innermost concentric electrode and is employed for disposing reference electrode 440, working electrodes 410 and 420, and dielectric layers 432, 442, 412, and 422 sequentially thereon. In view of the disclosure herein, it is again to be appreciated that other electrode and dielectric layer configurations may be employed in sensor configurations lacking central substrate 402. As such, the sensor configuration depicted in FIG. 5D should be considered illustrative in nature and non-limiting.

Accordingly, some embodiments of analyte sensors disclosed herein may comprise a sensor tail comprising at least a working electrode, a glucose-responsive active area comprising a glucose-responsive enzyme disposed upon a surface of the working electrode and a ketones-responsive active area disposed upon the surface of the working electrode and spaced apart from the glucose-responsive active area. The ketones-responsive active area comprises an enzyme system comprising at least two enzymes that are capable of acting in concert to facilitate detection of ketones. Each active area has an oxidation-reduction potential, and the oxidation-reduction potential of the glucose-responsive active area is sufficiently separated from the oxidation-reduction potential of the ketones-responsive active area to allow independent production of a signal from one of the glucose-responsive active area or the ketones-responsive active area.

When the glucose-responsive active area and the ketones-responsive active area are arranged upon a single working electrode in this manner, one of the active areas may be configured such that it can be interrogated separately to facilitate detection of each analyte, as described hereinafter. That is, either the glucose-responsive active area or the ketones-responsive active area may produce a signal independently of the other active area.

Some or other embodiments of analyte sensors disclosed herein may feature the glucose-responsive active area and the ketones-responsive active area upon the surface of different working electrodes. Such analyte sensors may comprise a sensor tail comprising at least a first working electrode and a second working electrode, a ketones-responsive active area disposed upon a surface of the first working electrode, a glucose-responsive active area comprising a glucose-responsive enzyme disposed upon a surface of the second working electrode, and a membrane having a first portion overcoating the ketones-responsive active area and a second portion overcoating the glucose-responsive active area, in which the first portion and the second portion have different compositions.

In particular embodiments, the first portion is multi-component and comprises at least a first membrane polymer and a second membrane polymer that differ from one another, and the second portion is homogeneous and comprises one of the first membrane polymer and the second membrane polymer.

According to various embodiments of the present disclosure, an electron transfer agent may be present in the glucose-responsive active area and the ketones-responsive active area in any of the illustrative sensor configurations disclosed herein. Suitable electron transfer agents may facilitate conveyance of electrons to the adjacent working electrode after either analyte undergoes an enzymatic oxidation-reduction reaction within the corresponding active area, thereby generating a current that is indicative of the presence of that particular analyte. The amount of current generated is proportional to the quantity of analyte that is present. Depending on the sensor configuration used, the electron transfer agents in the glucose-responsive active area and the ketones-responsive active area may be the same or different. For example, when the glucose-responsive active area and the ketones-responsive active area are disposed upon the same working electrode, the electron transfer agent within each active area may be different (e.g., chemically different such that the electron transfer agents exhibit different oxidation-reduction potentials). When multiple working electrodes are present, the electron transfer agent within each active area may be the same or different, since each working electrode may be interrogated separately.

According to various embodiments of the present disclosure, suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples of suitable electron transfer agents include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

Active areas suitable for detecting glucose and ketones may also comprise a polymer to which the electron transfer agents are covalently bound. Any of the electron transfer agents disclosed herein may comprise suitable functionality to promote covalent bonding to the polymer within the active areas. Suitable examples of polymer-bound electron transfer agents may include those described in U.S. Pat. Nos. 8,444,834, 8,268,143 and 6,605,201, the disclosures of which are incorporated herein by reference in their entirety. Suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. The polymer within each active area may be the same or different.

In particular embodiments of the present disclosure, the mass transport limiting membrane overcoating each active area may comprise at least a crosslinked polyvinylpyridine homopolymer or copolymer. The composition of the mass transport limiting membrane may be the same or different where the mass transport limiting membrane overcoats each active area. In particular embodiments, the portion of the mass transport limiting membrane overcoating the glucose-responsive active area may be single-component (contain a single membrane polymer) and the portion of the mass transport limiting membrane overcoating the ketones-responsive active area may be multi-component (contain two or more different membrane polymers, one of which is a polyvinylpyridine homopolymer or copolymer). The multi-component membrane may be present as a bilayer membrane or as a homogeneous admixture of the two or more membrane polymers. A homogeneous admixture may be deposited by combining the two or more membrane polymers in a solution and then depositing the solution upon a working electrode. In still more specific embodiments of the present disclosure, the glucose-responsive active area may be overcoated with a membrane comprising a polyvinylpyridine-co-styrene copolymer, and the ketones-responsive active area may be overcoated with a multicomponent membrane comprising polyvinylpyridine and polyvinylpyridine-co-styrene, either as a bilayer membrane or a homogeneous admixture.

The manner of covalent bonding between the electron transfer agent and the polymer comprising each active area is not considered to be particularly limited. Covalent bonding of the electron transfer agent to the polymer may take place by polymerizing a monomer unit bearing a covalently bound electron transfer agent, or the electron transfer agent may be reacted with the polymer separately after the polymer has already been synthesized. According to some embodiments, a bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, according to some or other various embodiments of the present disclosure, one or more of the enzymes within the active areas may be covalently bonded to the polymer. When an enzyme system comprising multiple enzymes is present in a given active area, all of the multiple enzymes may be covalently bonded to the polymer in some embodiments, and in other embodiments, only a portion of the multiple enzymes may be covalently bonded to the polymer. For example, one or more enzymes comprising an enzyme system may be covalently bonded to the polymer and at least one enzyme may be non-covalently associated with the polymer, such that the non-covalently bonded enzyme is physically entrained within the polymer. According to more specific embodiments, covalent bonding of the enzyme(s) to the polymer in a given active area may take place via a crosslinker introduced with a suitable crosslinking agent. Suitable crosslinking agents for reaction with free amino groups in the enzyme (e.g., with the free side chain amine in lysine) may include crosslinking agents such as, for example, polyethylene glycol diglycidyl ether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking of the enzyme to the polymer is generally intermolecular, but can be intramolecular in some embodiments.

The electron transfer agent and/or the enzyme(s) may be associated with the polymer in the active area through means other than covalent bonding as well. In some embodiments, the electron transfer agent and/or the enzyme(s) may be ionically or coordinatively associated with the polymer. For example, a charged polymer may be ionically associated with an oppositely charged electron transfer agent or enzyme(s). In still other embodiments, the electron transfer agent and/or the enzyme(s) may be physically entrained within the polymer without being bonded thereto. Physically entrained electron transfer agents and/or enzyme(s) may still suitably interact with a fluid to promote analyte detection without being substantially leached from the active areas.

In particular embodiments, the glucose-responsive enzyme in the glucose-responsive active area may be covalently bonded to a polymer in the glucose-responsive active area, in combination with an electron transfer agent that is also covalently bonded to the polymer.

In other particular embodiments, at least a portion of the enzymes in the enzyme system within the ketones-responsive active area may be covalently bonded to a polymer in the ketones-responsive active area, in combination with an electron transfer agent that is also covalently bonded to the polymer. One suitable enzyme system that may be suitable to facilitate detection of ketones is β-hydroxybutyrate dehydrogenase (NADH), nicotinamide adenine dinucleotide ($NAD^+$), and diaphorase (see FIG. 2A). In particular embodiments of the present disclosure, the β-hydroxybutyrate dehydrogenase and diaphorase may be covalently bonded to the polymer in the ketones-responsive active area, and the $NAD^+$ may be non-covalently associated with the polymer. The polymer within the ketones-responsive active area may be chosen such that outward diffusion of the $NAD^+$ is limited. The membrane polymer overcoating the ketones-responsive active area may similarly limit outward diffusion of $NAD^+$ to promote a reasonable sensor lifetime (days to weeks) while still allowing sufficient inward ketones diffusion to promote detection. In still further embodiments, the components of the foregoing enzyme system may be covalently bonded or non-covalently associated with the polymer in the ketones-responsive active area as described previously, in combination with an electron transfer agent that is also covalently bonded to the polymer.

The glucose-responsive and ketones-responsive active areas in the analyte sensors disclosed herein may comprise one or more discrete spots (e.g., one to about ten spots, or even more discrete spots), which may range in size from about 0.01 $mm^2$ to about 1 $mm^2$, although larger or smaller individual spots within the active areas are also contemplated herein. Active areas defined as continuous bands around a cylindrical electrode are also possible in the disclosure herein.

In more specific embodiments, analyte sensors of the present disclosure may comprise a sensor tail that is configured for insertion into a tissue. Suitable tissues are not considered to be particularly limited and are addressed in more detail above. Similarly, considerations for deploying a sensor tail at a particular position within a tissue are addressed above.

In embodiments wherein the glucose-responsive active area and the ketones-responsive active area are arranged upon a single working electrode, the oxidation-reduction potential associated with the glucose-responsive active area may be separated from the oxidation-reduction potential of the ketones-responsive active area by at least about 100 mV, or by at least about 150 mV, or by at least about 200 mV. The upper limit of the separation between the oxidation-reduction potentials is dictated by the working electrochemical window in vivo. By having the oxidation-reduction potentials of the two active areas sufficiently separated in magnitude from one another, an electrochemical reaction make take place within one of the two active areas (i.e., within the glucose-responsive active area or the ketones-responsive active area) without substantially inducing an electrochemical reaction within the other active area. Thus, a signal from one of the glucose-responsive active area or the ketones-responsive active area may be independently produced at or above its corresponding oxidation-reduction potential (the lower oxidation-reduction potential) but below the oxidation-reduction potential of the other of the glucose-responsive active area and the ketones-responsive active area (the higher oxidation-reduction potential). At or above the oxidation-reduction potential (the higher oxidation-reduction potential) of the other active area that was not previously interrogated, in contrast, electrochemical reactions may occur within both the glucose-responsive active area and the ketones-responsive active area. As such, the resulting signal at or above the higher oxidation-reduction potential may include a signal contribution from both the glucose-responsive active area and the ketones-responsive active area, and the observed signal is a composite signal. The signal contribution from one active area (either the glucose-responsive active area or the ketones-responsive active area) at or above its oxidation-reduction potential may then be determined by subtracting from the composite signal the signal obtained solely from either the glucose-responsive active area or the ketones-responsive active area at or above its corresponding oxidation-reduction potential.

In more specific embodiments, the glucose-responsive active area and the ketones-responsive active area may contain different electron transfer agents when the active areas are located upon the same working electrode, so as to afford oxidation-reduction potentials that are sufficiently separated in magnitude from one another. More specifically, the glucose-responsive active area may comprise a first electron transfer agent and the ketones-responsive active area may comprise a second electron transfer agent, with the first and second electron transfer agents being different. The metal center and/or the ligands present in a given electron transfer agent may be varied to provide sufficient separation of the oxidation-reduction potentials within the two active areas, according to various embodiments of the present disclosure.

Ideally, glucose-responsive active areas and ketones-responsive active areas located upon a single working electrode may be configured to attain a steady state current rapidly upon operating the analyte sensor at a given potential. Rapid attainment of a steady state current may be promoted by choosing an electron transfer agent for each active area that changes its oxidation state quickly upon being exposed to a potential at or above its oxidation-reduction potential. Making the active areas as thin as possible may also facilitate rapid attainment of a steady state current. For example, suitable thicknesses for the glucose-responsive active area and ketones-responsive active area may range from about 0.1 microns to about 10 microns. In some or other embodiments, combining a conductive material such as, for example, carbon nanotubes, graphene, or metal nanoparticles within one or more of the active areas may promote rapid attainment of a steady state current. Suitable amounts of conductive particles may range from about 0.1% to about 50% by weight of the active area, or from about 1% to about 50% by weight, or from about 0.1% to about 10% by weight, or from about 1% to about 10% by weight. Stabilizers may also be employed to promote response stability.

It is also to be appreciated that the sensitivity (output current) of the analyte sensors toward each analyte may be varied by changing the coverage (area or size) of the active areas, the areal ratio of the active areas with respect to one another, the identity, thickness and/or composition of a mass transport limiting membrane overcoating the active areas. Variation of these parameters may be conducted readily by one having ordinary skill in the art once granted the benefit of the disclosure herein.

Detection methods for assaying glucose and ketones employing analyte sensors featuring a glucose-responsive active area and a ketones-responsive active area upon a single working electrode may comprise: exposing an analyte sensor to a fluid comprising at least one of glucose and ketones. The analyte sensor comprises a sensor tail comprising at least a working electrode, particularly a single working electrode, and at least a glucose-responsive active area and a ketones-responsive active area disposed upon a surface of the working electrode and space apart from the glucose-responsive active area. The glucose-responsive active area comprises a glucose-responsive enzyme and a polymer, and the ketones-responsive active area comprises an enzyme system comprising two or more enzymes that are capable of acting in concert to facilitate detection of ketones. Each active area has an oxidation-reduction potential, and the oxidation-reduction potential of a first active area (e.g., either the glucose-responsive active area or the ketones-responsive active area) is sufficiently separated from the oxidation-reduction potential of the other of the glucose-responsive active area or the ketones-responsive active area to allow production of a signal from the first active area independent of production of a signal from the other active area. The methods additionally comprise: obtaining a first signal at or above a lower of the oxidation-reduction potential and the second oxidation-reduction potential but below a higher of the first oxidation-reduction potential and the second oxidation-reduction potential, such that the first signal is proportional to a concentration of one of glucose or ketones in the fluid; obtaining a second signal at or above a higher of the first oxidation-reduction potential and the second oxidation-reduction potential, such that the second signal is a composite signal comprising a signal contribution from the glucose-responsive active area and a signal contribution from the ketones-responsive active area; and subtracting the first signal from the second signal to obtain a difference signal, the difference signal being proportional to a concentration of one of glucose and ketones.

In more specific embodiments, the oxidation-reduction potential associated with the first active area may be separated from the oxidation-reduction potential of the second active area by at least about 100 mV, or by at least about 150 mV, or by at least about 200 mV in order to provide sufficient separation for independent production of a signal from the first active area. In particular, the oxidation-reduction potentials of the first active area and the second active area may be separated by about 100 mV to about 500 mV, or about 100 mV to about 400 mV, or about 100 mV to about 300 mV.

In some embodiments, the signals associated with each active area may be correlated to a corresponding concentration of glucose or ketones by consulting a lookup table or calibration curve for each analyte. A lookup table for each analyte may be populated by assaying multiple samples having known analyte concentrations and recording the sensor response at each concentration for each analyte. Similarly, a calibration curve for each analyte may be determined by plotting the analyte sensor response for each analyte as a function of the concentration and determining a suitable calibration function over the calibration range (e.g., by regression, particularly linear regression).

A processor may determine which sensor response value in a lookup table is closest to that measured for a sample having an unknown analyte concentration and then report the analyte concentration accordingly. In some or other embodiments, if the sensor response value for a sample having an unknown analyte concentration is between the recorded values in the lookup table, the processor may interpolate between two lookup table values to estimate the analyte concentration. Interpolation may assume a linear concentration variation between the two values reported in the lookup table. Interpolation may be employed when the sensor response differs a sufficient amount from a given value in the lookup table, such as variation of about 10% or greater.

Likewise, according to some or other various embodiments, a processor may input the sensor response value for a sample having an unknown analyte concentration into a corresponding calibration function. The processor may then report the analyte concentration accordingly.

Detection methods for assaying glucose and ketones employing analyte sensors featuring a glucose-responsive active area and a ketones-responsive active area upon separate working electrodes may comprise: exposing an analyte sensor to a fluid comprising at least one of glucose and ketones. The analyte sensor comprises a sensor tail comprising at least a first working electrode and second working electrode, a ketones-responsive active area disposed upon a surface of the first working electrode, a glucose-responsive active area disposed upon a surface of the second working electrode, and a membrane having a first portion overcoating the ketones-responsive active area and a second portion overcoating the glucose-responsive active area. The glucose-responsive active area comprises a glucose-responsive enzyme, and the ketones-responsive active area comprises an enzyme system comprising at least two enzymes that are capable of acting in concert to facilitate detection of ketones.

In particular embodiments, the first portion may be multi-component and comprise at least a first membrane polymer and a second membrane polymer that differ from one another, and the second portion may be homogeneous and comprise one of the first membrane polymer and the second membrane polymer. As such, the membrane overcoating the glucose-responsive active area differs in composition from the multi-component membrane overcoating the ketones-responsive active area.

The methods additionally comprise applying a potential to the first working electrode and the second working electrode, obtaining a first signal at or above an oxidation-reduction potential of the glucose-responsive active area, in which the first signal is proportional to a concentration of glucose in the fluid, obtaining a second signal at or above an oxidation-reduction potential of the ketones-responsive active area, in which the second signal is proportional to a concentration of ketones in the fluid, and correlating the first signal to the concentration of glucose in the fluid and the second signal to the concentration of ketones in the fluid.

The first portion of the membrane may comprise an admixture of membrane polymers in some embodiments of the present disclosure or comprise a bilayer membrane or other membrane structure having at least two membrane layers in other embodiments of the present disclosure. When the first portion of the membrane comprises a bilayer membrane, the bilayer membrane may comprise a first membrane polymer disposed upon the ketones-responsive active area, and a second membrane polymer disposed upon the first membrane polymer. The homogeneous membrane overcoating the glucose-responsive active area may comprise the second membrane polymer. That is, the first membrane polymer may be disposed directly upon the ketones-responsive active area, and the second membrane polymer may be disposed upon the first membrane polymer and upon the glucose-responsive active area. Thus, the first portion of the membrane may be thicker than the second portion of the membrane. As discussed above, bilayer membranes and homogeneous membranes of this type may be deposited by dip coating of particular electrode configurations in some embodiments of the present disclosure. In particular embodiments of the present disclosure, the first portion of the membrane may comprise polyvinylpyridine (PVP) and polyvinylpyridine-co-styrene, and second portion of the membrane may comprise polyvinylpyridine-co-styrene.

According to more specific embodiments, the first signal and the second signal maybe measured at different times. Thus, in such embodiments, a potential may be alternately applied to the first working electrode and the second working electrode. In other specific embodiments, the first signal and the second signal may be measured simultaneously via a first channel and a second channel, in which case a potential may be applied to both electrodes at the same time. In either case, the signal associated with each active area may then be correlated to the concentration of glucose and ketones using a lookup table or a calibration function in a similar manner to that discussed above.

Embodiments disclosed herein include:

A. Analyte sensors responsive to glucose and ketones. The analyte sensors comprise: a sensor tail comprising at least a working electrode; a glucose-responsive active area comprising a glucose-responsive enzyme disposed upon a surface of the working electrode; a ketones-responsive active area disposed upon the surface of the working electrode and spaced apart from the glucose-responsive active area, the ketones-responsive active area comprising an enzyme system comprising at least two enzymes that are capable of acting in concert to facilitate detection of ketones; wherein each active area has an oxidation-reduction potential, and the oxidation-reduction potential of the glucose-responsive active area is sufficiently separated from the oxidation-reduction potential of the ketones-responsive active area to allow independent production of a signal from one of the glucose-responsive active area or the ketones-responsive active area.

B. Methods for assaying glucose and ketones using a single analyte sensor. The methods comprise: exposing an analyte sensor to a fluid comprising at least one of glucose and ketones; wherein the analyte sensor comprises a sensor tail comprising at least a working electrode, a glucose-responsive active area having a first oxidation-reduction potential disposed upon a surface of the working electrode, and a ketones-responsive active area having a second oxidation-reduction potential disposed upon the surface of the working electrode and spaced apart from the glucose-responsive active area; wherein the glucose-responsive active area comprises a glucose-responsive enzyme, the ketones-responsive active area comprises an enzyme system comprising at least two enzymes that are capable of acting in concert to facilitate detection of ketones, and the first oxidation-reduction potential and the second oxidation-reduction potential are sufficiently separated from one another to allow independent production of a signal from one of the glucose-responsive active area or the ketones-responsive active area; obtaining a first signal at or above a lower of the first oxidation-reduction potential and the second oxidation-reduction potential but below a higher of the first oxidation-reduction potential and the second oxidation-reduction potential, the first signal being proportional to a concentration of one of glucose or ketones in the fluid; obtaining a second signal at or above a higher of the first oxidation-reduction potential and the second oxidation-reduction potential, the second signal being a composite signal comprising a first signal contribution from the glucose-responsive active area and a second signal contribution from the ketones-responsive active area; and subtracting the first signal from the second signal to obtain a difference signal, the difference signal being proportional to a concentration of one of glucose or ketones in the fluid.

C. Analyte sensors responsive to glucose and ketones and having two working electrodes. The analyte sensors comprise: a sensor tail comprising at least a first working electrode and a second working electrode; a glucose-responsive active area comprising a glucose-responsive enzyme disposed upon a surface of the first working electrode; a ketones-responsive active area disposed upon a surface of the second working electrode, the ketones-responsive active area comprising an enzyme system comprising at least two enzymes that are capable of acting in concert to facilitate detection of ketones; a first membrane overcoating the ketones-responsive active area, and a second membrane overcoating the glucose-responsive active area; wherein the first membrane and the second membrane have differing permeability values.

D. Methods for assaying glucose and ketones using a single analyte sensor having two working electrodes. The methods comprise: exposing an analyte sensor to a fluid comprising at least one of glucose and ketones; wherein the analyte sensor comprises a sensor tail comprising at least a first working electrode and second working electrode, a glucose-responsive active area disposed upon a surface of the first working electrode, a ketones-responsive active area disposed upon a surface of the second working electrode, and a first membrane overcoating the ketones-responsive active area, and a second membrane overcoating the glucose-responsive active area; wherein the first membrane and the second membrane have differing permeability values; wherein the glucose-responsive active area comprises a glucose-responsive enzyme, and the ketones-responsive active area comprises an enzyme system comprising at least two enzymes that are capable of acting in concert to facilitate detection of ketones; applying a potential to the first working electrode and the second working electrode; obtaining a first signal at or above an oxidation-reduction potential of the glucose-responsive active area, the first signal being proportional to a concentration of glucose in the fluid; obtaining a second signal at or above an oxidation-reduction potential of the ketones-responsive active area, the second signal being proportional to a concentration of ketones in the fluid; and correlating the first signal to the concentration of glucose in the fluid and the second signal to the concentration of ketones in the fluid.

Each of embodiments A-D may have one or more of the following additional elements in any combination:

Element 1: wherein the sensor tail is configured for insertion into a tissue.

Element 2: wherein the oxidation-reduction potential of the glucose-responsive active area is separated from the oxidation-reduction potential of the ketones-responsive active area by at least about 100 mV.

Element 3: wherein the glucose-responsive active area comprises a first electron transfer agent covalently bonded to a polymer in the first active area and the ketones-responsive active area comprises a second electron transfer agent covalently bonded to a polymer in the second active area, the first and second electron transfer agents being different.

Element 4: wherein the glucose-responsive enzyme is covalently bonded to the polymer in the glucose-responsive active area and one or more of the at least two enzymes in the enzyme system are covalently bonded to the polymer in the ketones-responsive active area.

Element 5: wherein the analyte sensor further comprises a mass transport limiting membrane overcoating the glucose-responsive active area and the ketones-responsive active area.

Element 6: wherein the fluid is a biological fluid and the analyte sensor is exposed to the biological fluid in vivo.

Element 7: wherein a mass transport limiting membrane overcoats the glucose-responsive active area and the ketones-responsive active area.

Element 8: wherein the first membrane is a multi-component membrane overcoating the ketones-responsive active area, the multi-component membrane comprising at least a first membrane polymer and a second membrane polymer that differ from one another, and the second membrane is a homogeneous membrane overcoating the glucose-responsive active area and differing in composition from the multi-component membrane, the homogeneous membrane comprising one of the first membrane polymer and the second membrane polymer.

Element 9: wherein the multi-component membrane comprises a bilayer membrane.

Element 10: wherein the first membrane polymer is disposed directly upon the ketones-responsive active area, the second membrane polymer is disposed upon the first membrane polymer to define the bilayer membrane, and the homogenous membrane comprises the second membrane polymer.

Element 11: wherein the multi-component membrane comprises an admixture of the first membrane polymer and the second membrane polymer.

Element 12: wherein the multi-component membrane comprises polyvinylpyridine and polyvinylpyridine-co-styrene, and the homogeneous membrane comprises polyvinylpyridine-co-styrene.

Element 13: wherein the glucose-responsive active area and the ketones-responsive active area each comprise an electron-transfer agent that is covalently bonded to a polymer in each of the glucose-responsive active area and the ketones-responsive active area.

Element 14: wherein the first signal and the second signal are measured at different times.

Element 15: wherein the first signal and the second signal are obtained simultaneously via a first channel and a second channel.

By way of non-limiting example, exemplary combinations applicable to A and B include: 1 and 2; 1 and 3; 1 and 4; 1 and 5; 2 and 3; 2 and 4; 2 and 5; 3 and 4; 3 and 5; 4 and 5; 1 and 6; 2 and 6; 3 and 6; 4 and 6; and 5 and 6.

By way of further non-limiting example, exemplary combinations applicable to C and D include: 1 and 8; 4 and 8; 1 and 9; 4 and 9; 1 and 10; 4 and 10; 1 and 11; 4 and 11; 1 and 12; 4 and 12; 1 and 13; 4 and 13; 1 and 14; 4 and 14; 1 and 15; 4 and 15; 4 and 9; 4, 9 and 10; 4 and 11; 4 and 12; 4 and 13; 4 and 14; 4 and 15; 8 and 9; 8-10; 8 and 11; 8 and 12; 8 and 13; 8 and 14; 8 and 15; 9 and 10; 9 and 11; 9 and 12; 9 and 13; 9 and 14; 9 and 15; 11 and 12; 11 and 13; 11 and 14; 11 and 15; 12 and 13; 12 and 14; 12 and 15; 13 and 14; 13 and 15; and 14 and 15.

Additional embodiments disclosed herein include:

A'. Analyte sensors responsive to glucose and ketones. The analyte sensors comprise: a sensor tail comprising at least a first working electrode and a second working electrode; a ketones-responsive active area disposed upon a surface of the first working electrode, the ketones-responsive active area comprising an enzyme system comprising at least two enzymes that are capable of acting in concert to facilitate detection of ketones; a glucose-responsive active area comprising a glucose-responsive enzyme disposed upon a surface of the second working electrode; and a membrane having a first portion overcoating the ketones-responsive active area and a second portion overcoating the glucose-responsive active area; wherein the first portion and the second portion have different compositions.

B'. Methods for assaying glucose and ketones using a single analyte sensor. The methods comprise: exposing an analyte sensor to a fluid comprising at least one of glucose and ketones; wherein the analyte sensor comprises a sensor tail comprising at least a first working electrode and second working electrode, a ketones-responsive active area disposed upon a surface of the first working electrode, a glucose-responsive active area disposed upon a surface of the second working electrode, and a membrane having a first portion overcoating the ketones-responsive active area and a second portion overcoating the glucose-responsive active area; wherein the first portion and the second portion have different compositions; wherein the glucose-responsive active area comprises a glucose-responsive enzyme, and the ketones-responsive active area comprises an enzyme system comprising at least two enzymes that are capable of acting in concert to facilitate detection of ketones; applying a potential to the first working electrode and the second working electrode; obtaining a first signal at or above an oxidation-reduction potential of the glucose-responsive active area, the first signal being proportional to a concentration of glucose in the fluid; obtaining a second signal at or above an oxidation-reduction potential of the ketones-responsive active area, the second signal being proportional to a concentration of ketones in the fluid; and correlating the first signal to the concentration of glucose in the fluid and the second signal to the concentration of ketones in the fluid.

Element 1': wherein the first portion is multi-component and comprises at least a first membrane polymer and a second membrane polymer that differ from one another.

Element 2': wherein the second portion is homogenous and comprises one of the first membrane polymer and the second membrane polymer.

Element 3': wherein the first portion comprises at least two membrane layers.

Element 4': wherein the first membrane polymer is disposed directly upon the ketones-responsive active area, and the second membrane polymer is disposed upon the first membrane polymer and upon the glucose-responsive active area.

Element 5': wherein the first portion of the membrane is thicker than the second portion of the membrane.

Element 6': wherein the first portion of the membrane comprises polyvinylpyridine and polyvinylpyridine-co-styrene, and the second portion of the membrane comprises polyvinylpyridine-co-styrene.

Element 7': wherein the first portion of the membrane comprises an admixture of the first membrane polymer and the second membrane polymer.

Element 8': wherein the first portion and the second portion define a continuous membrane overcoating the ketones-responsive active area and the glucose-responsive active area.

Element 9': wherein the sensor tail is configured for insertion into a tissue.

Element 10': wherein the glucose-responsive active area and the ketones-responsive active area each comprise an electron-transfer agent that is covalently bonded to a polymer in each of the glucose-responsive active area and the ketones-responsive active area.

Element 11': wherein the glucose-responsive enzyme is covalently bonded to the polymer in the glucose-responsive active area and one or more of the at least two enzymes in the enzyme system are covalently bonded to the polymer in the ketones-responsive active area.

Element 12': wherein the fluid is a biological fluid and the analyte sensor is exposed to the biological fluid in vivo.

Element 13': wherein the first signal and the second signal are measured at different times.

Element 14': wherein the first signal and the second signal are obtained simultaneously via a first channel and a second channel.

By way of non-limiting example, exemplary combinations applicable to A' and B' include: 1' and 2'; 1' and 3'; 1', 3' and 4'; 1'-4'; 1' and 5'; 1' and 6'; 1' and 7'; 1' and 8'; 1' and 9'; 1' and 10'; 1' and 11'; 2' and 3'; 3' and 4'; 2'-4'; 3' and 5'; 3' and 6'; 3' and 7'; 3' and 8'; 3' and 9'; 3' and 10'; 3' and 11'; 3'-5'; 3', 4' and 6'; 3' and 4'; 3', 4' and 8'; 3', 4' and 9'; 3', 4' and 10'; 3', 4' and 11'; 6' and 7'; 7' and 8'; 7' and 9'; 7' and 10'; 7' and 11'; 8' and 9'; 8' and 10'; 8' and 11'; 10' and 11', any of which may be in further combination with element 12'; element 13' or element 14'. Other exemplary combinations applicable to B' include any one of elements 1'-11' in combination with one or more of element 12', element 13' or element 14'; 12' and 13'; and 12' and 14'.

To facilitate a better understanding of the embodiments described herein, the following examples of various representative embodiments are given. In no way should the following examples be read to limit, or to define, the scope of the invention.

EXAMPLES

A poly(vinylpyridine)-bound transition metal complex having the structure shown in Formula 1 was prepared. Further details concerning this transition metal complex and electron transfer therewith is provided in commonly owned U.S. Pat. No. 6,605,200, which was incorporated by reference above. The subscripts for each monomer represent illustrative atomic ratios and are not indicative of any particular monomer ordering.

Formula 1

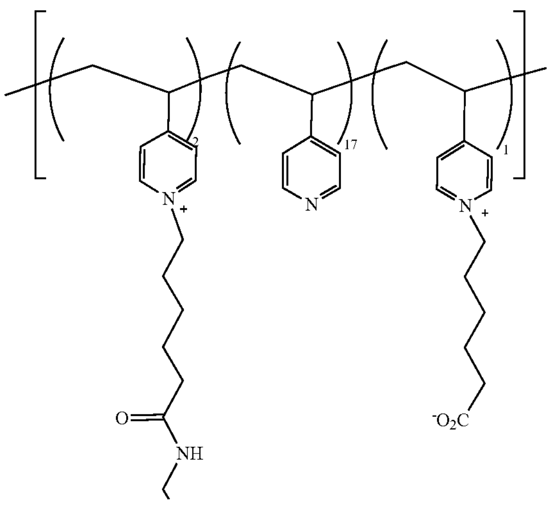

-continued

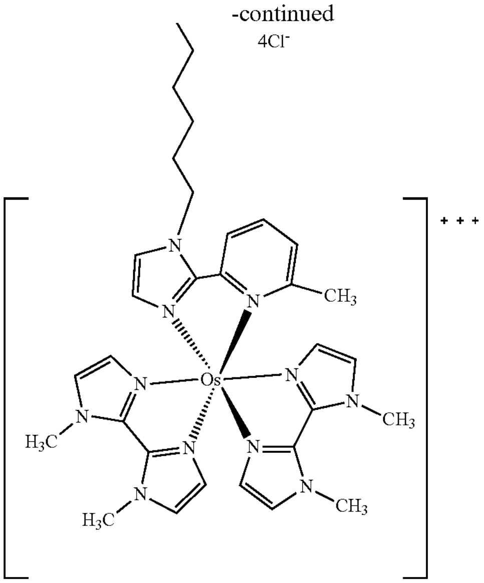

Example 1: Detection of Ketones Using an Analyte Sensor Having Diaphorase and p-Hydroxybutyrate Dehydrogenase Acting in Concert. For this example, the enzyme system of FIG. 2A was used to facilitate detection of ketones. The spotting formulation shown in Table 1 below was coated onto a carbon working electrode. Deposition was performed to place six spots, each having an area of around 0.01 $mm^2$, upon the working electrode. Following deposition, the working electrode was cured overnight at 25° C. Thereafter, a homogeneous PVP membrane was applied to the working electrode via dip coating using a coating solution formulated with 4 mL of 100 mg/mL PVP, 0.2 mL of 100 mg/mL PEGDGE400 (PEGDGE with a molecular weight of approximately 400), and 0.0132 mL of 100 mg/mL polydimethylsiloxane (PDMS). Membrane curing was performed for 24 hours at 25° C., followed by 48 hours at 56° C. in desiccated vials.

TABLE 1

| β-Hydroxybutyrate Dehydrogenase (HBDH) in 10 mM MES Buffer at pH = 5.5 | |
|---|---|
| Component | Concentration (mg/mL) |
| HBDH | 8 |
| Diaphorase | 4 |
| Albumin | 8 |
| $NAD^+$ | 8 |
| Formula 1 Polymer | 8 |
| PEGDGE400 | 4 |

Figure 6:
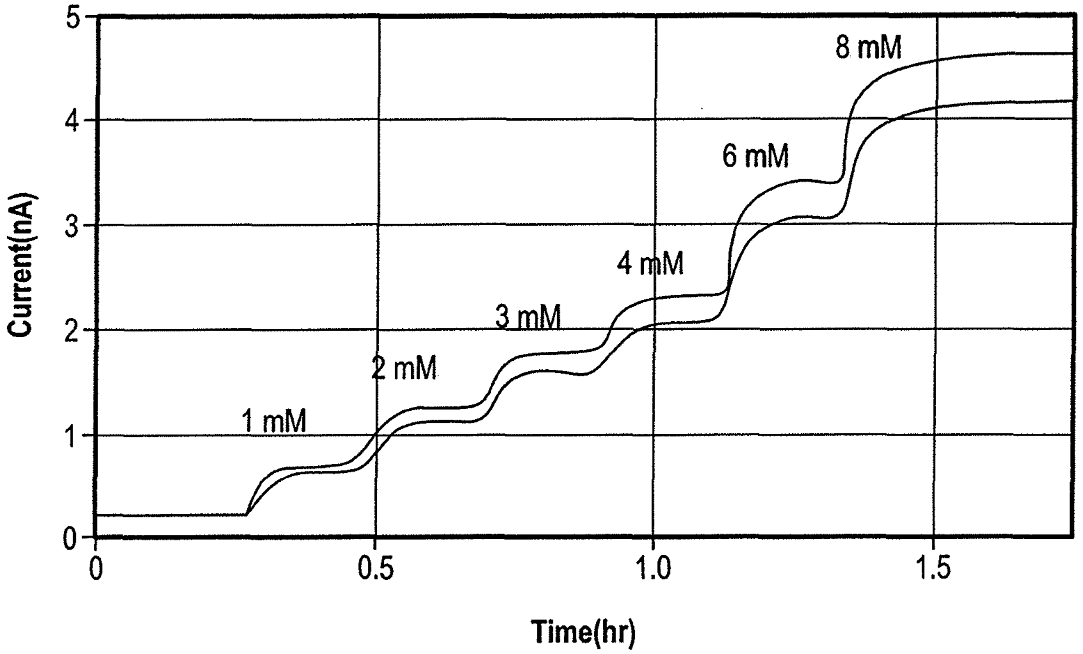
FIG. 6 shows four replicates of the response for an electrode containing diaphorase, $NAD^+$, and β-hydroxybutyrate dehydrogenase when exposed to varying β-hydroxybutyrate concentrations.
Figure 7:
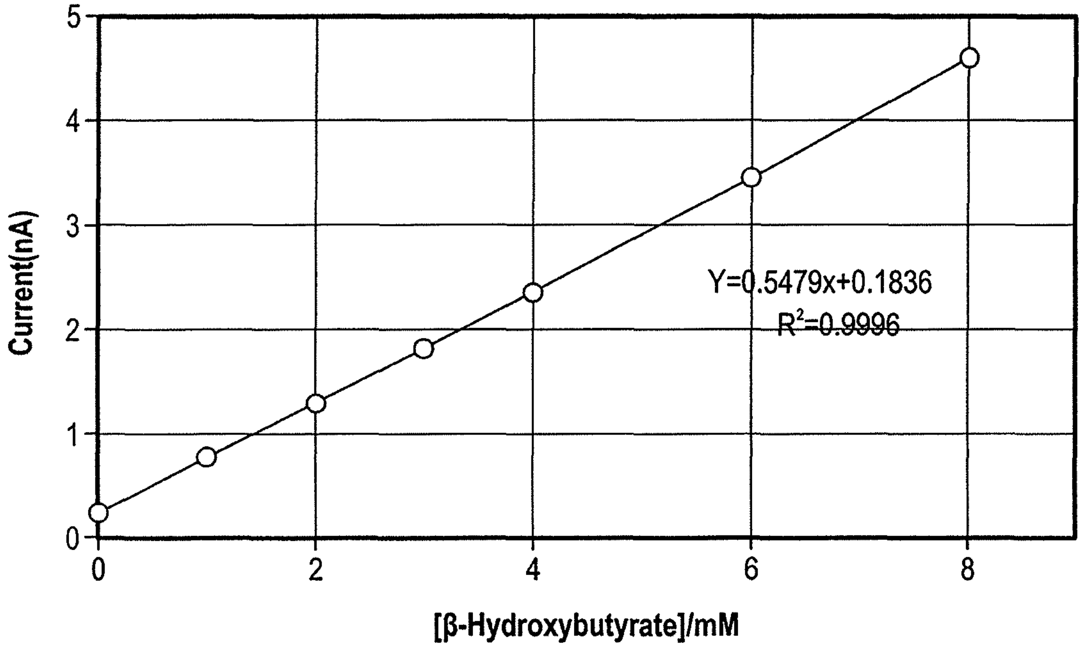
FIG. 7 shows an illustrative plot of average current response versus β-hydroxybutyrate concentration for the electrodes of FIG. 6.
Figure 8:
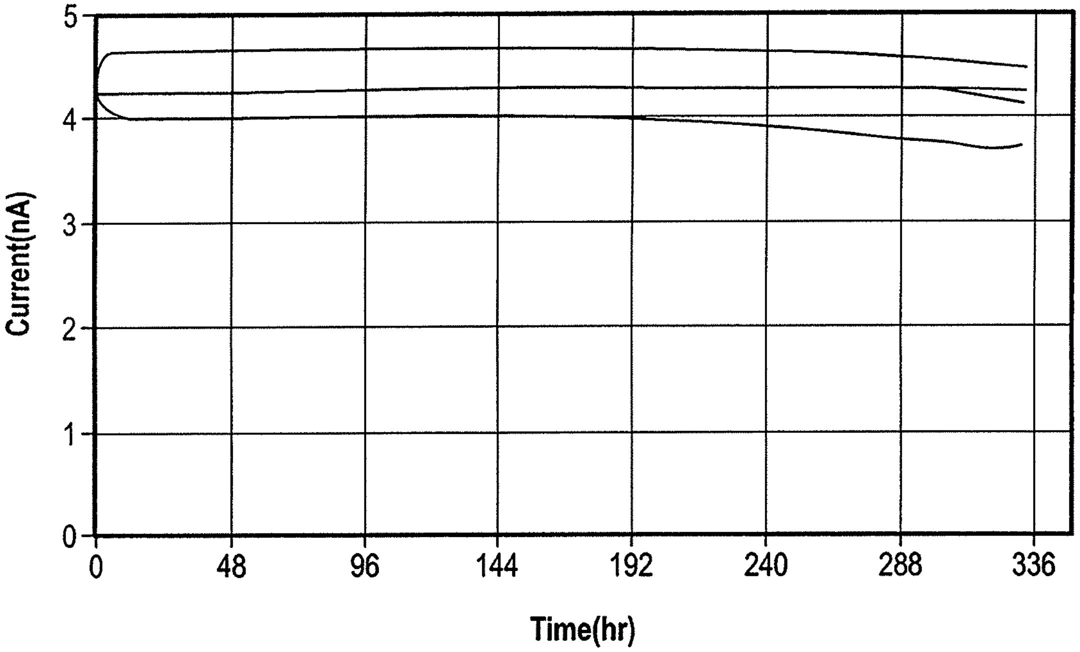
FIG. 8 shows an illustrative plot of current response for the electrodes of FIG. 6 when exposed to 8 mM of β-hydroxybutyrate in 100 mM PBS at 33° C. for 2 weeks.

Ketone analyses were conducted by immersing the electrode in 100 mM PBS buffer (pH=7.4) at 33° C. and introducing various amounts of β-hydroxybutyrate (0, 1, 2, 3, 4, 6 and 8 mM total β-hydroxybutyrate addition) as a ketones surrogate. FIG. 6 shows four replicates of the response for an electrode containing diaphorase, $NAD^+$, and β-hydroxybutyrate dehydrogenase when exposed to varying β-hydroxybutyrate concentrations. Only two traces are apparent in FIG. 6 due to overlap of the signal response for the four sensors tested. As shown, the current response increased over the course of several minutes following exposure to a new β-hydroxybutyrate concentration before stabilizing thereafter. FIG. 7 shows an illustrative plot of average current response versus β-hydroxybutyrate concentration for the electrodes of FIG. 6. The ketone sensors also exhibited a stable response over extended measurement times, as shown in FIG. 8. FIG. 8 shows an illustrative plot of current response for the electrodes of FIG. 6 when exposed to 8 mM of β-hydroxybutyrate in 100 mM PBS at 33° C. for 2 weeks. The mean signal loss over the measurement period was only 3.1%.

Example 2: Detection of Glucose and Ketones Using an Analyte Sensor Having a Glucose-Responsive Active Area and a Ketones-Responsive Active Area on Separate Working Electrodes. For this example, an analyte sensor was prepared with a glucose-responsive active area comprising glucose oxidase deposited upon a first working electrode and a ketones-responsive active area comprising diaphorase and β-hydroxybutyrate dehydrogenase deposited upon a second working electrode. The two working electrodes were carbon electrodes disposed upon opposing faces of a planar dielectric substrate.

The glucose-responsive active area was deposited upon the first working electrode using the glucose oxidase formulation specified in Table 2 below. Active area deposition was conducted by placing five discrete, separate spots, each having an area of approximately 0.01 $mm^2$, upon the working electrode. Following deposition, the working electrode was cured overnight at 25° C.

TABLE 2

| Glucose Oxidase (GOX) Formulation in 10 mM HEPES Buffer at pH = 8 | | | |
|---|---|---|---|
| Component | Initial Concentration (mg/mL) | Added Volume (mL) | Final Concentration (mg/mL) |
| GOX | 60 | 0.41 | 24.6 |
| Formula 1 Polymer | 60 | 0.34 | 20.4 |
| PEGDE400 | 60 | 0.25 | 15 |

The ketones-responsive active area was deposited upon the second working electrode using the diaphorase/β-hydroxybutyrate formulation specified in Table 1 above. Active area deposition and curing was conducted as in Example 1 above, except five sensing spots were deposited in this instance. Curing of the ketones-responsive active area and the glucose-responsive active area was conducted at the same time.

Following deposition of the active areas, a bilayer membrane was deposited upon the ketones-responsive active area as follows. A PVP membrane was first deposited upon the ketones-responsive active area using via a modified slot coating procedure. The PVP membrane in this example was deposited from a coating solution formulated with 4 mL of 160 mg/mL PVP, 0.133 mL of 100 mg/mL PEGDGE400, and 0.0132 mL of 100 mg/mL PDMS. Curing was then performed for 24 hours at 25° C. The slot coating procedure was conducted using a syringe pump to pump the coating solution from a nozzle located a small distance above a row of sensor tails. The coating solution was pumped at a constant rate while moving the nozzle at a fixed rate across the row of sensor tails. Parameters such as flow rates, nozzle diameter, the rate of nozzle movement, the distance between the nozzle and the sensor tails, the solution viscosity, the temperature, and the solvent were varied to afford a membrane having a desired thickness.

Thereafter, the entire assembly (i.e., both working electrodes, the glucose-responsive active area, the PVP coating upon the working electrode containing the ketones-responsive active area, and the counter and reference electrodes) was dip coated to introduce a crosslinked polyvinylpyridine-co-styrene membrane polymer thereon. The membrane polymer coating the entire assembly was deposited using 4 mL of polyvinylpyridine-co-styrene in 80:20 ethanol:HEPES buffer (140 mg/mL), 0.2 mL PEGDGE400 in 80:20 ethanol:HEPES buffer (100 mg/mL), and 0.0132 mL of aminopropyl-terminated polydimethylsiloxane (PDMS) in ethanol (100 mg/mL). Curing was again performed for 24 hours at 25° C., followed by 48 hours at 56° C. in a desiccated environment. Thus, a homogeneous membrane (polyvinylpyridine-co-styrene) was deposited upon the glucose-responsive active area and a bilayer membrane (inner layer of PVP and outer layer of polyvinylpyridine-co-styrene) was deposited upon the ketones-responsive active area.

Figure 9:
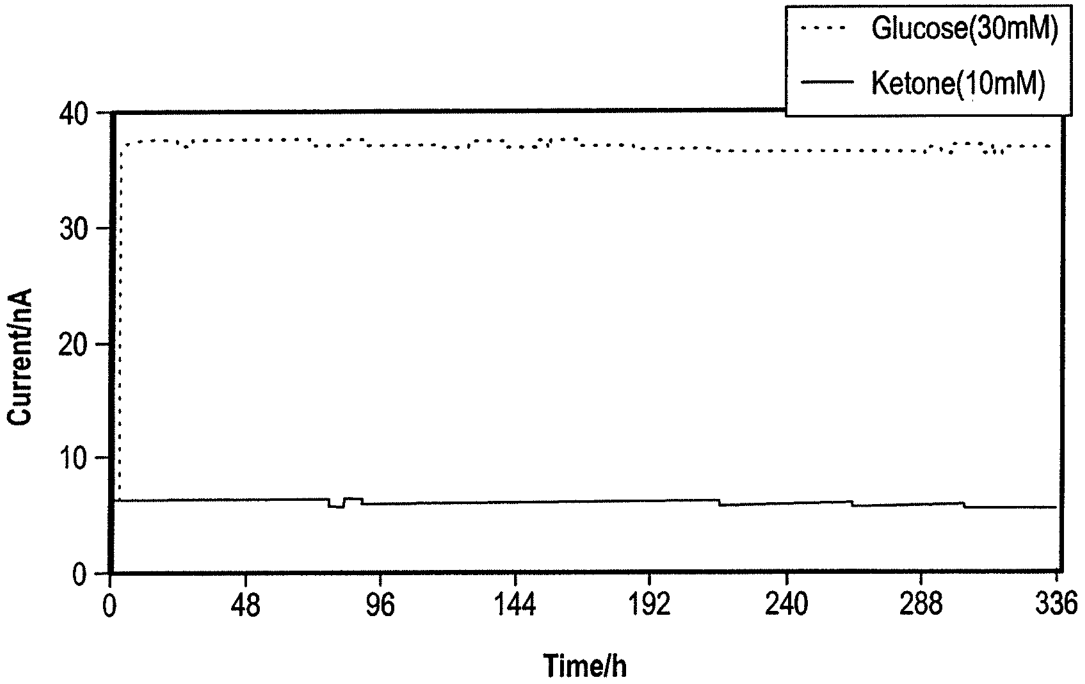
FIG. 9 shows an illustrative plot of the response for an analyte sensor containing a glucose-responsive active area and a ketones-responsive active area disposed upon separate working electrodes following exposure to 30 mM glucose and 10 mM ketones.

The analyte sensor was used to assay for glucose and ketones simultaneously in 100 mM PBS at 37° C. In a first experiment, the sensor was exposed for 2 weeks at 37° C. to a 100 mM PBS solution containing 30 mM glucose and 10 mM β-hydroxybutyrate (ketones surrogate). The sensor was held at +40 mV relative to Ag/AgCl for this experiment. FIG. 9 shows an illustrative plot of the response for an analyte sensor containing a glucose-responsive active area and a ketones-responsive active area disposed upon separate working electrodes following exposure to 30 mM glucose and 10 mM ketones. As shown, the response of the analyte sensor remained very steady over the observation period for both analytes.

Figure 10:
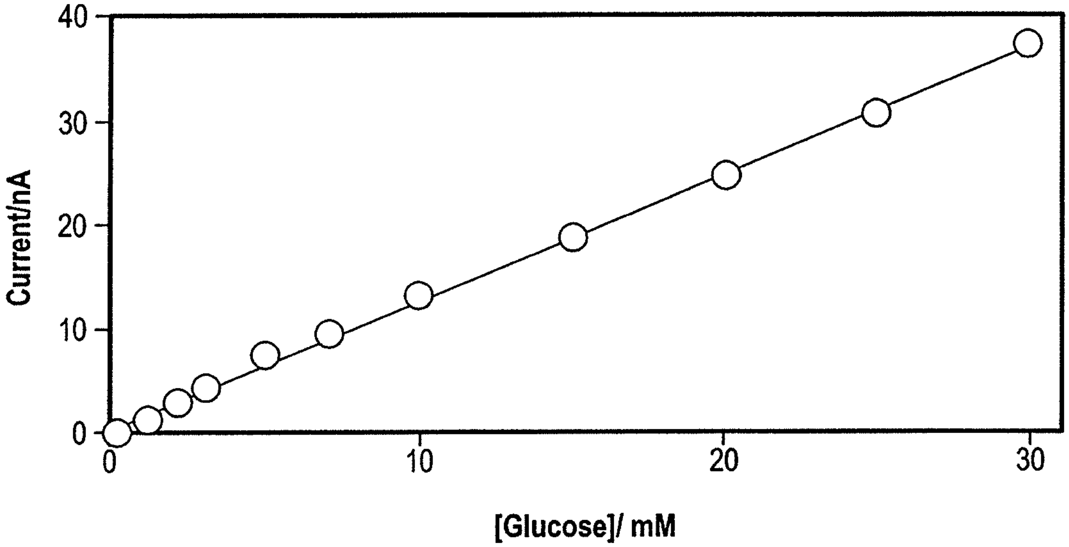
FIGS. 10-12 show illustrative plots of the response of an analyte sensor containing a glucose-responsive active area and a ketones-responsive active area to varying concentrations of glucose and β-hydroxybutyrate.
Figure 11:
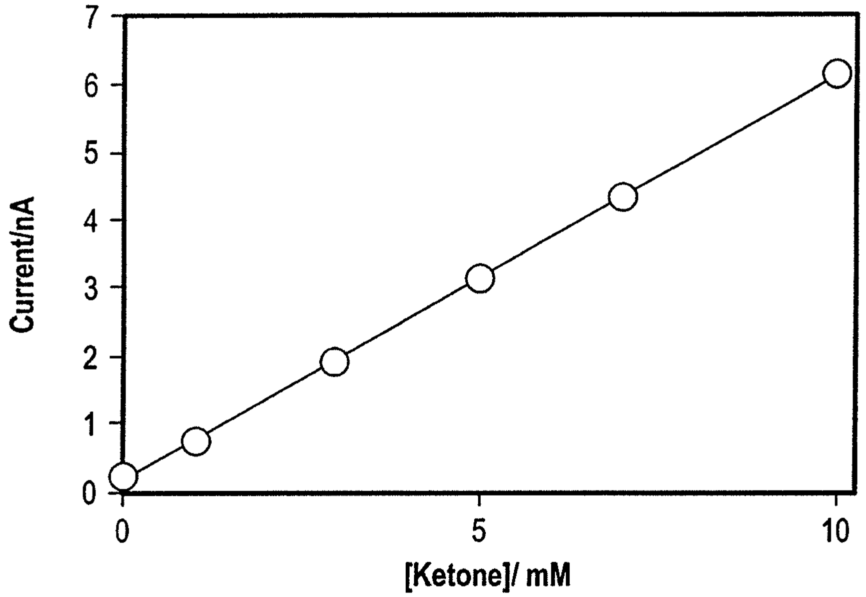
Figure 12:
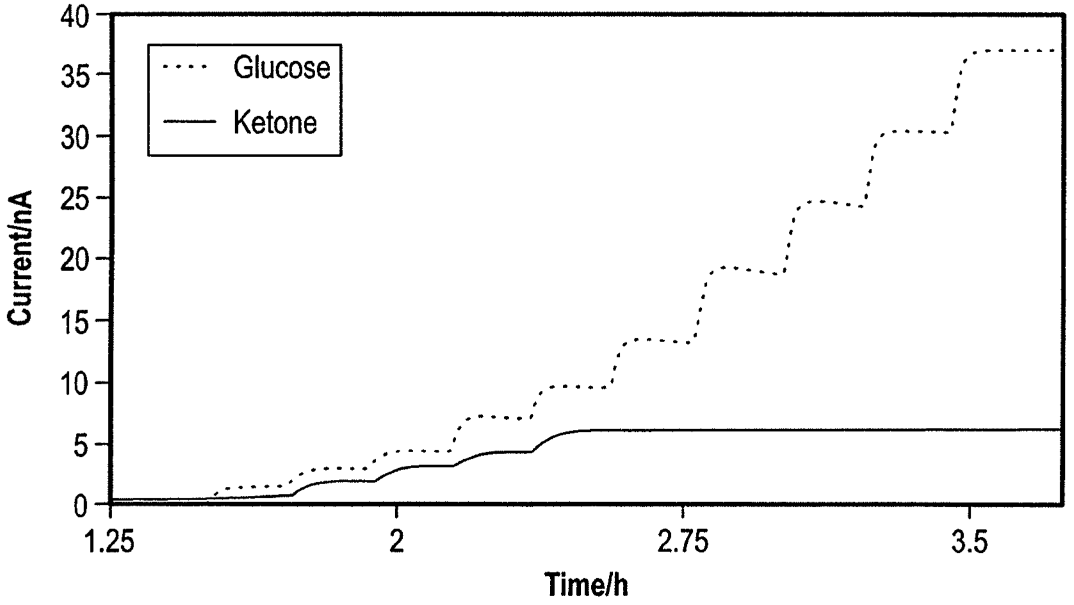

Next, glucose and β-hydroxybutyrate were added incrementally to 100 mM PBS at 37° C. to determine the response of the analyte sensor toward each analyte. The sensor was again held at +40 mV relative to Ag/AgCl for this test. Glucose was added over a concentration range of 0-30 mM, and β-hydroxybutyrate was added over a concentration range of 0-10 mM. Each analyte was added simultaneously at concentrations of 10 mM or under. Above 10 mM, only additional glucose was added to the solution, with 10 mM representing the maximum ketones concentration tested. FIGS. 10-12 show illustrative plots of the analyte sensor response to varying concentrations of glucose and β-hydroxybutyrate. As shown in FIGS. 10 and 11, the analyte sensor afforded a linear response toward both analytes over the tested concentration ranges. As shown in FIG. 12, the sensor response was rapid for both analytes and remained stable at a given analyte concentration.

Example 3: Detection of Ketones Using an Analyte Sensor Having NADH Oxidase and β-Hydroxybutyrate Dehydrogenase Acting in Concert. For this example, the enzyme system of FIG. 2B was used to facilitate detection of ketones. The spotting formulation shown in Table 3 below was coated onto either a carbon working electrode or a carbon nanotube working electrode. Coating was conducted by hand in 3 passes to coat the entirety of the sensor tip. The mean active area was 3.0 $mm^2$ for the carbon working electrode and 7.6 $mm^2$ for the carbon nanotube working electrode. Following deposition, the working electrodes were cured overnight at 25° C. Thereafter, a PVP membrane was applied to the working electrodes via dip coating using a coating solution formulated with 4 mL of 100 mg/mL PVP and 0.2 mL of 100 mg/mL PEGDGE400. Membrane curing was performed for 24 hours at 25° C.

TABLE 3

| β-Hydroxybutyrate Dehydrogenase (HBDH) in 10 mM MES Buffer at pH = 5.5 | |
|---|---|
| Component | Concentration (mg/mL) |
| HBDH | 8 |
| Albumin | 8 |
| $NAD^+$ | 8 |
| NADHOx | 8 |
| PVI | 8 |
| PEGDGE400 | 4 |

Figure 13A:
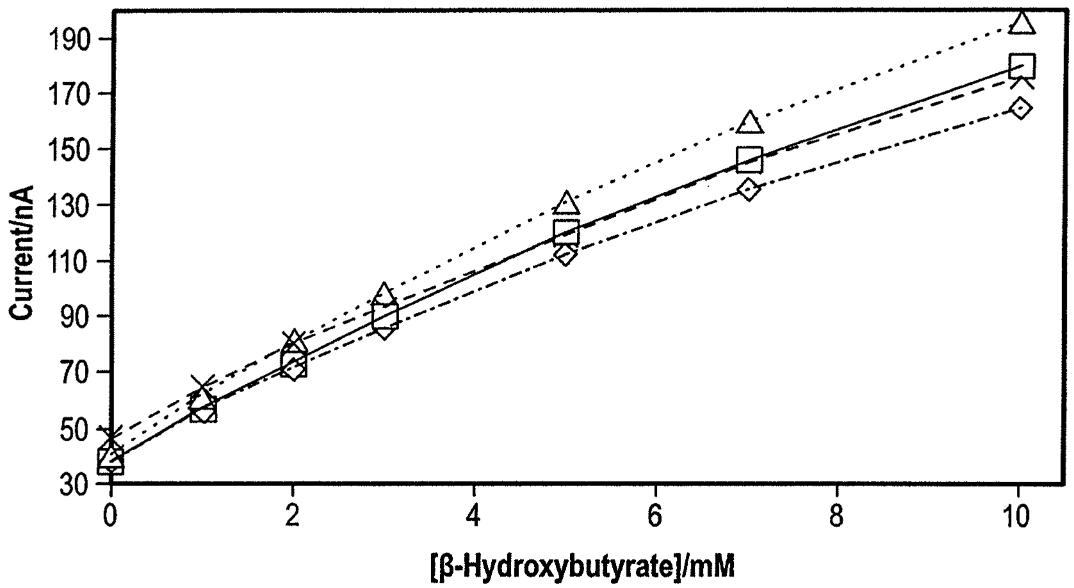
FIGS. 13A and 13B show four replicates of the response for an electrode containing NADHOx, $NAD^+$, and β-hydroxybutyrate dehydrogenase when exposed to varying β-hydroxybutyrate concentrations.
Figure 13B:
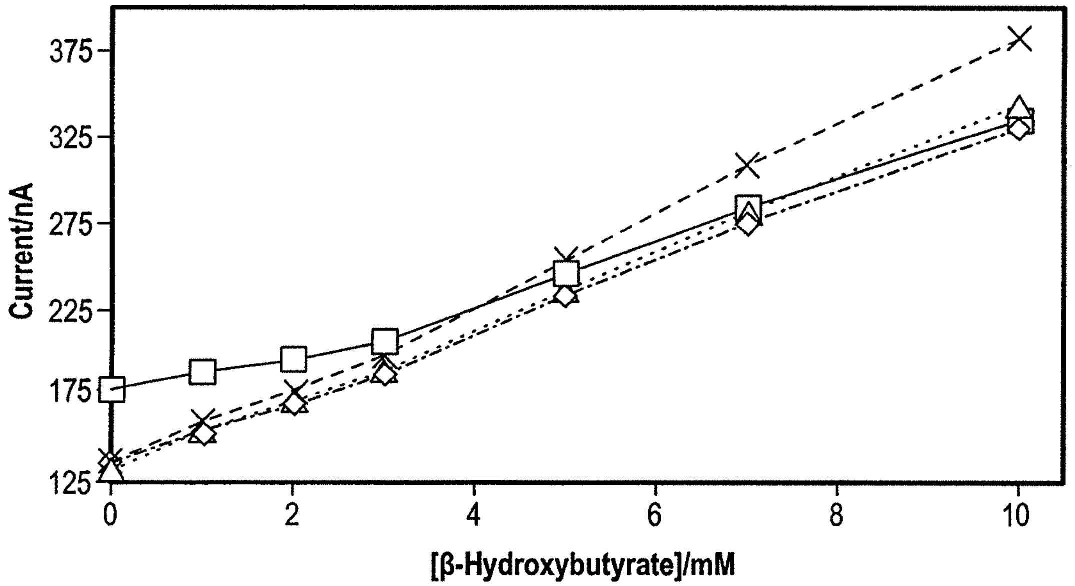
Figure 14:
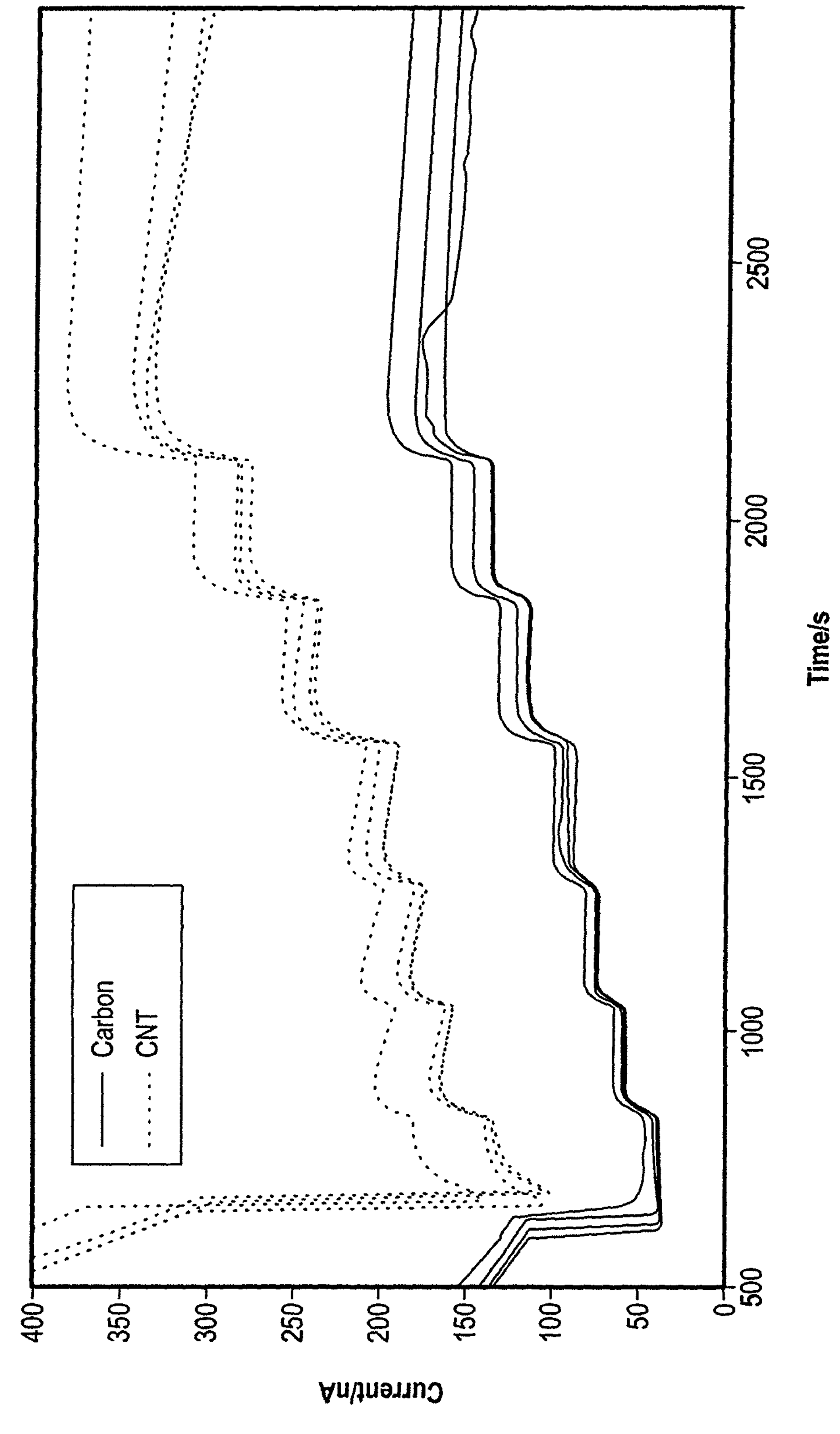
FIG. 14 shows an illustrative plot of current response versus time for an electrode containing NADHOx, $NAD^+$, and β-hydroxybutyrate dehydrogenase after exposure to increasing β-hydroxybutyrate dehydrogenase concentrations.

Ketone analyses were conducted as set forth in Example 1. FIGS. 13A and 13B show four replicates of the response for an electrode containing NADHOx, $NAD^+$, and β-hydroxybutyrate dehydrogenase when exposed to varying β-hydroxybutyrate concentrations. FIG. 13A shows the current response for a carbon working electrode, and FIG. 13B shows the current response for a carbon nanotube working electrode. As shown, the current response for both types of working electrode increased as the β-hydroxybutyrate concentration increased up to a concentration of 10 mM. FIG. 14 shows an illustrative plot of current response versus time for an electrode containing NADHOx, $NAD^+$, and β-hydroxybutyrate dehydrogenase after exposure to increasing β-hydroxybutyrate dehydrogenase concentrations. As shown, the current increased rapidly after adding β-hydroxybutyrate dehydrogenase and stabilized thereafter.

Example 4: Detection of Ketones Using an Analyte Sensor Containing Poly-1,10-phenanthroline-5,6-dione and p-Hydroxybutyrate Dehydrogenase. For this example, the enzyme system of FIG. 2C was used to facilitate detection of ketones. The spotting formulation shown in Table 4 below was coated onto either a carbon working electrode or a carbon nanotube working electrode. Coating and curing of the spotting formulation and the PVP membrane was conducted as specified in Example 3. The mean active area was 3.0 $mm^2$ for the carbon working electrode and 7.6 $mm^2$ for the carbon nanotube working electrode.

TABLE 4

| β-Hydroxybutyrate Dehydrogenase (HBDH) in 10 mM MES Buffer at pH = 5.5 | |
|---|---|
| Component | Concentration (mg/mL) |
| HBDH | 8 |
| Albumin | 8 |
| $NAD^+$ | 8 |
| 1,10-phenanthroline-5,6-dione | 8 |
| PVI | 8 |
| PEGDGE400 | 4 |

Figure 15A:
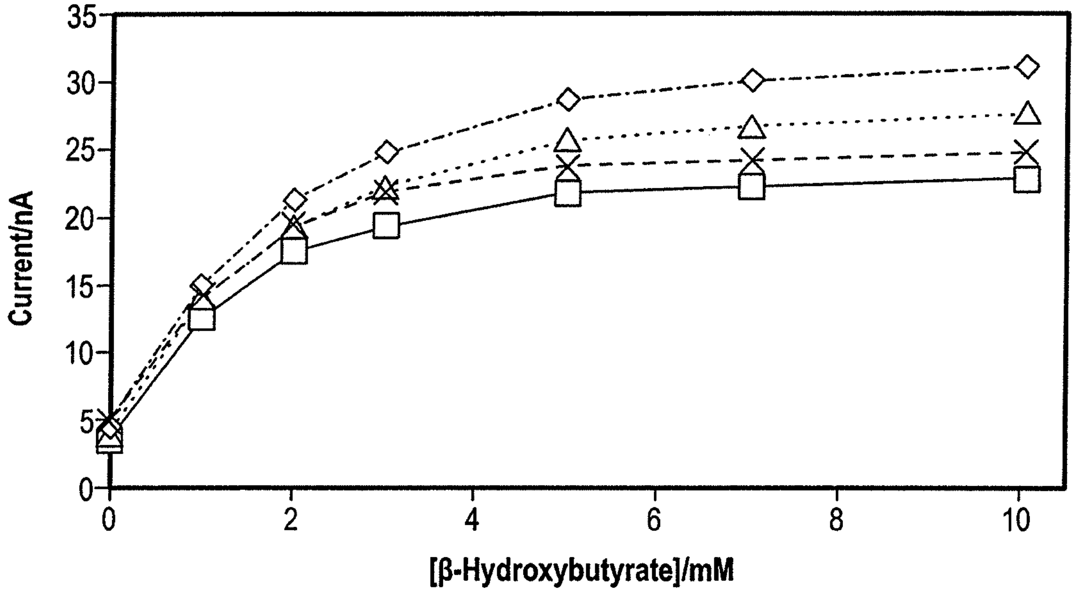
FIG. 15A shows the current response for a carbon working electrode.
Figure 15B:
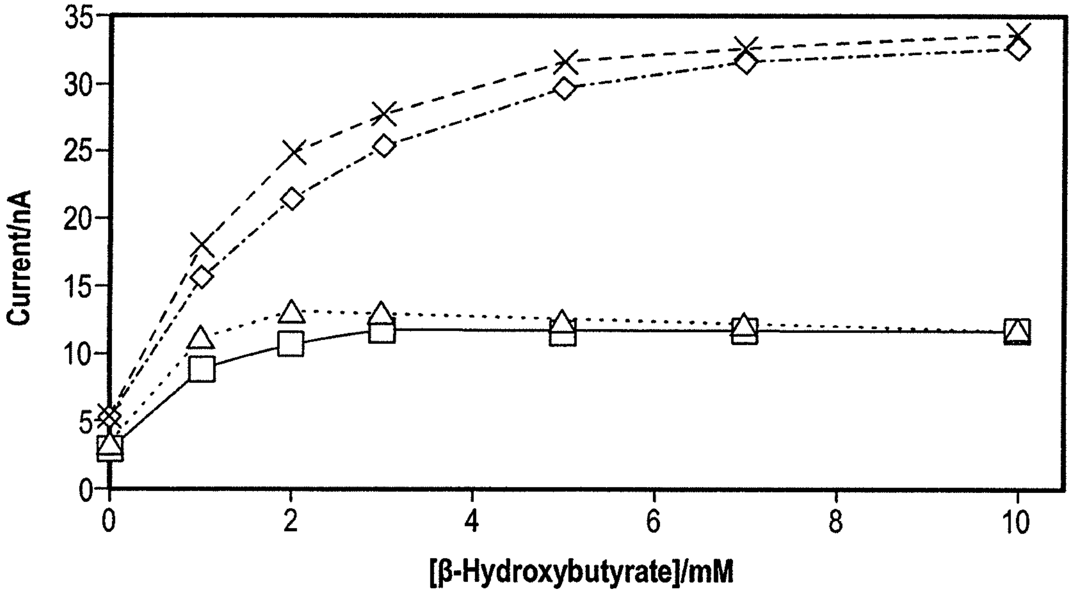
FIG. 15B shows the current response for a carbon nanotube working electrode, each containing poly-1,10-phenanthroline-5,6-dione and β-hydroxybutyrate dehydrogenase.

Ketone analyses were conducted as set forth in Example 1. FIGS. 15A and 15B show four replicates of the response for an electrode containing poly-1,10-phenanthroline-5,6-dione and β-hydroxybutyrate dehydrogenase when exposed to varying β-hydroxybutyrate concentrations. FIG. 15A shows the current response for a carbon working electrode, and FIG. 15B shows the current response for a carbon nanotube working electrode. As shown, the current response for both types of working electrode increased as the β-hydroxybutyrate concentration increased up to a concentration of about 2 mM before the response began to flatten.

Analyte Sensor Ignition Lock

Vehicle fail safes, such as ignition locks, are sometimes used to prevent an operator from operating a vehicle when impaired or otherwise not in a condition to safely operate the vehicle. Operating the vehicle while impaired could potentially present significant dangers to the operator and the public. One common type of ignition lock is designed to prevent drunk driving and, more specifically, to prevent individuals from operating a vehicle while intoxicated through alcohol use. Such lock devices connect a breath-alcohol analyzer or optical sensor to the vehicle's ignition system, and the driver must successfully pass a blood alcohol level test before the vehicle can be started.

Intoxication is one type of impairment or condition that an operator may experience that renders the operator unfit or unable to operate a vehicle. However, other impairments and conditions can also afflict an operator and should also be monitored closely to ensure the operator does not operate a vehicle while impaired. For example, an operator with diabetes and driving while hypoglycemic (i.e., low blood sugar) could potentially undergo light-headedness, confusion, headache, loss of consciousness, seizures, and delayed reflexes, any of which could endanger his/her own life and those in the vehicle or in the vicinity of the vehicle.

Analyte monitoring systems, have been developed to facilitate long-term monitoring of analytes in bodily fluid (e.g., blood). Some analyte monitoring systems are designed to detect and monitor levels of blood glucose, which can be helpful in treating diabetic conditions. Other analyte monitoring systems, however, are designed to detect and monitor other analytes present in an operator's bodily fluid, and abnormal analyte levels detected in an operator may be indicative that the operator is currently unfit to safely operate a vehicle.

The following discussion describes an analyte monitoring and vehicle control system used to prevent operation of a vehicle when operator analyte levels cross a predetermined threshold. Having the sensor control device 102 (FIG. 1) properly deployed allows a user to intelligently track and monitor bodily fluid analyte levels and trends. When some analyte levels surpass certain thresholds, physical or cognitive impairment may ensue that renders a user unfit to safely operate a vehicle. In such instances, the user should take appropriate action to bring analyte levels back into safe ranges prior to attempting to operate a vehicle. In some cases, however, a user may feel perfectly fine to operate a vehicle but nonetheless have unsafe analyte levels that could suddenly trigger the onset of a dangerous physical impairment. In such cases, it may be advantageous to have a failsafe system in place that prevents or warns the user from operating a vehicle and potentially placing self and/or others in danger.

Figure 16:
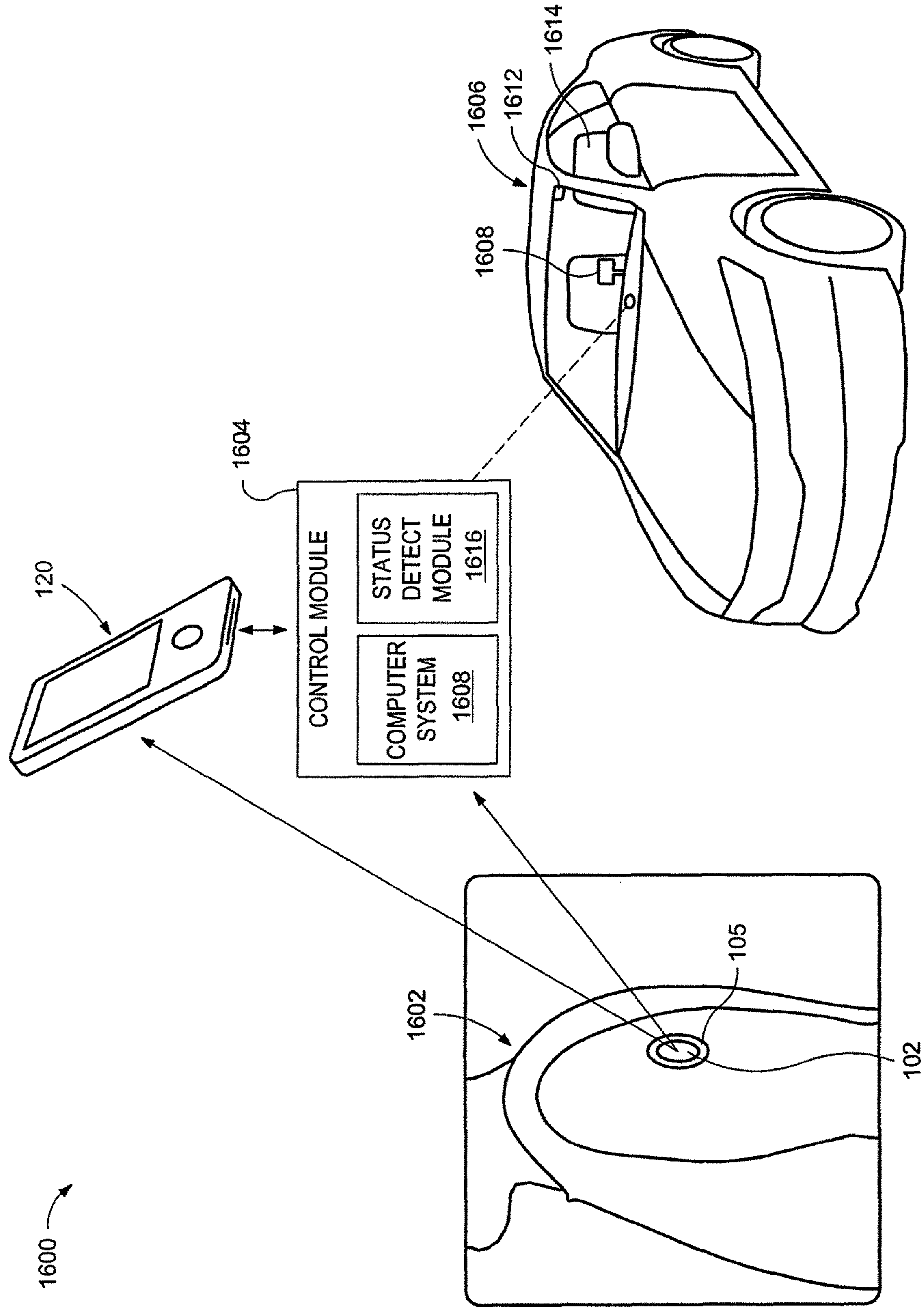
FIG. 16 is a schematic diagram of an example analyte monitoring and vehicle control system, according to one or more embodiments of the present disclosure.

FIG. 16 is a schematic diagram of an example analyte monitoring and vehicle control system 1600, according to one or more embodiments of the present disclosure. As illustrated, the analyte monitoring and vehicle control system 1600 (hereafter "the system 1600) includes the sensor control device 102, which may be deployed on a user or "operator" 3202 and otherwise delivered to a target monitoring location on the body of the operator 1602, such as the back of an arm. As discussed above, the sensor control device 102 includes the sensor 104 (FIG. 1), and when properly deployed, the sensor 104 is positioned transcutaneously within the skin to detect and monitor analytes present within a bodily fluid of the operator 1602. The adhesive patch 105 (FIG. 1) applied to the bottom of the sensor control device 102 adheres to the skin to secure the sensor control device 102 in place during operation.

While the system 1600 is described herein as including the on-body sensor control device 102 to detect and report analyte levels, the system 1600 may alternatively incorporate an ex vivo analyte sensor (e.g., a self-monitoring blood glucose "SMBG" meter), without departing from the scope of the disclosure. Accordingly, the term "sensor control device" should be interpreted herein to include not only on-body sensor systems, as generally described above, but also traditional, hand-held sensor systems.

As illustrated, the system 1600 may further include the reader device 120, and the sensor control device 102 may be in communication with the reader device 120 via a local communication path or link to provide analyte concentration data automatically, periodically, or as desired by the operator 1602. The reader device 120 may be in communication with a control module 1604, which is in communication with the electrical system of a vehicle 1606 and powered by the vehicle battery or otherwise powered by a separate battery. In such embodiments, data transmitted to the reader device 120 from the sensor control device 102 may be subsequently transmitted by the reader device 120 to the control module 1604 for processing. In other embodiments, however, the sensor control device 102 may communicate directly with the control module 1604 via any wireless communication protocol, such as BLUETOOTH®. In such embodiments, the reader device 120 may or may not be necessary in the system 1600.

In the illustrated embodiment, the vehicle 1606 is depicted as an automobile. As used herein, however, the term "vehicle" is used broadly and is meant to include any kind of transportation vehicle that can be operated by a human user or "operator," but can also include autonomous vehicles used to transport humans. Examples of the vehicle 1606 include, but are not limited to, any type of automobile, truck, sport utility vehicle, aircraft, watercraft, spacecraft, and or any other means of transportation, or combinations thereof.

The control module 1604 may include a communications interface to communicate information to/from the sensor control device 102 and/or the reader device 120. In the case of an exemplary BLUETOOTH®-enabled sensor control device 102 and/or reader device 120, a pairing mode may be entered into when the sensor control device 102 approaches the vehicle 1606. Upon pairing, the control module 1604 may be programmed and configured to automatically detect the presence of and establish communication with the sensor control device 102 and/or the reader device 120. For example, when the operator 1602 approaches or enters the vehicle 1606, the control module 1604 may automatically detect the presence of the sensor control device 102 and enable communication therebetween or with the reader device 120.

In some embodiments, the control module 1604 may be in communication with a vehicle user interface 1608 included in the vehicle 1606, such as an infotainment system, a touchscreen display, or an information display. In such embodiments, the control module 1604 may visually communicate with the operator 1602 via the vehicle user interface 1608 and may also be able to audibly communicate with the operator 1602 via the audio speakers included in the vehicle 1606. In other embodiments, however, the control module 1604 may be configured to communicate with the reader device 120 to be able to communicate with the operator 1602.

As illustrated, the control module 1604 may be or otherwise include a computer system 1610 configured and otherwise programmed to control various operations and/or systems of the vehicle 1606 based on real-time measured analyte levels of the operator 1602 as obtained by the sensor control device 102. Operation of the vehicle 1606 is controlled, disabled, or modified by either disabling one or more critical systems of the vehicle 1606 or by activating warning systems in the vehicle 1606. When the real-time measured analyte levels of the operator 1602 are within a predetermined safe range, then it may be considered safe for the operator 1602 to operate the vehicle 1606. When the real-time measured analyte levels of the operator 1602 fall outside the predetermined safe range or cross a predetermined threshold, however, the computer system 1610 may then be programmed to control, disable, or modify operation of the vehicle 1606.

In some embodiments, for example, the computer system 1610 may be configured to disable various critical vehicle systems when detected analyte levels of the operator 1602 fall outside of a predetermined range or otherwise cross a predetermined threshold, thus progressively and safely disabling operation of the vehicle when identifying the operator 1602 as impaired for safe operation of the vehicle 1606. Critical vehicle systems of the vehicle 1606 that may be disabled include the ignition system (e.g., energy switching/control system), the transmission system (or gear box), the fuel system, energy supply system (e.g., a battery, capacitor, conversion/reaction cell, etc.). When elevated or lowered (unsafe) analyte levels are detected, the computer system 1610 may prevent the critical vehicle systems from functioning or operating. Consequently, the operator 1602 will be unable to start or operate the vehicle 1606, thereby preventing the operator 1602 from placing themselves and/or others in danger.

In other embodiments, or in addition thereto, the computer system 1610 may be configured to activate various non-critical vehicle systems when detected analyte levels of the operator 1602 surpass or cross a predetermined threshold. Non-critical vehicle systems that may be activated include, for example, the vehicle horn, the vehicle lights, or an audible warning system installed in the vehicle 1606. In such embodiments, activation of the non-critical vehicle systems may alert law enforcement and others (e.g., operators of adjacent vehicles, bystanders, pedestrians, etc.) of an operator 1602 that may be driving in an impaired condition, thus allowing law enforcement to quickly address any issues related thereto and placing others on notice of a potentially dangerous situation.

In yet other embodiments, or in addition thereto, the computer system 1610 may be configured to automatically place a phone call to one or more emergency contacts when analyte levels of the operator 1602 fall outside of a predetermined safe operating range or otherwise cross a predetermined threshold. In such embodiments, the computer system 1610 may operate through the reader device 120 (e.g., a cellular phone) or a cellular or satellite communication system incorporated into the vehicle 1606 (e.g., OnStar®). In other embodiments, or in addition thereto, the computer system 1610 may be configured to automatically send a message (e.g., text or SMS message, email, etc.) to an emergency contact when analyte levels of the operator 1602 fall outside of a predetermined safe operating range or otherwise cross a predetermined threshold. Example emergency contacts include, but are not limited to, a spouse, a parent, medical personnel (e.g., a doctor), a hospital, 911, or any combination thereof.

In some embodiments, the system 1600 may further include one or more proximity sensors 1612 configured to detect the presence of the operator 1602 and, more particularly, the sensor control device 102. In such embodiments, the proximity sensor(s) 1612 may be configured to monitor the general area of the driver's seat 1614 within the vehicle 1606. If the sensor control device 102 is detected within the area of the driver's seat 1614 by the proximity sensor(s) 1612, that may provide a positive indication that the operator 1602 is in the driver's seat 1614 and potentially attempting to operate the vehicle 1606. In such cases, a signal may be sent to the control module 1604 alerting the computer system 1610 that the operator 1602 is in the vehicle 1606 and potentially attempting to operate the vehicle 1606. If the real-time measured analyte levels of the operator 1602 are within a predetermined safe range or below a predetermined level, then the computer system 1610 may allow the operator 1602 to operate the vehicle 1606. When the real-time measured analyte levels of the operator 1602 fall outside the predetermined safe range or cross a predetermined threshold, however, the computer system 1610 may control, disable, or modify operation of the vehicle 1606, as generally described above. As will be appreciated, the proximity sensor(s) 1612 may be advantageous in preventing operation of the vehicle 1606 only when the impaired operator 1602 is in the driver's seat 1614 and ready to operate the vehicle 1606. Consequently, a user wearing the sensor control device 102 is able to ride as a passenger in the vehicle 1606 in any state without affecting operation of the control module 1604 or the vehicle 1606.

In some embodiments, the control module 1604 may further include a vehicle status detection module 1616 configured to detect the current status of the vehicle 1606, including whether the vehicle 1606 is currently moving or is stationary. In addition, the vehicle status detection module 1616 may be configured to determine whether or not the motor in the vehicle 1606 is currently operating or is stopped. In one or more embodiments, the vehicle status detection module 1616 may provide a status signal to the control module 1604, and the control module 1604 can then use the status signal to determine what vehicle operations should be activated or disabled when the real-time measured analyte levels of the operator 1602 fall outside the predetermined safe range or cross a predetermined threshold. For example, when the status signal indicates that the vehicle 1606 is stationary, the control module 1604 can disable the vehicle fuel system, transmission system, ignition system, or any combination thereof. In contrast, when the status signal indicates that the vehicle 1606 is moving, the control module 1604 can activate the vehicle horn, flash the vehicle lights, or activate an audible warning to the operator 1602 and/or those around the operator 1602 that the operator 1602 is impaired.

In some embodiments, once the operator 1602 enters the vehicle 1606 or when the control module 1604 pairs with the sensor control device 102 and/or the reader device 120, an app may be launched on the reader device 120 or the vehicle user interface 1608, and a digital dashboard may appear on the reader device 120 and/or the vehicle user interface 1608 that depicts current analyte levels, trend, historical data, and projected analyte levels. If the current analyte levels fall outside of a predetermined safe operating range, however, the computer system 1610 may be programmed to disable one or more critical vehicle systems to prevent the operator 1602 from operating the vehicle 1606. In such embodiments, a visual or audible alert may be issued by the control module 1604 to inform the operator 1602 as to why the vehicle 1606 is not starting. More particularly, a visual alert (e.g., a written message) may be generated and displayed on the reader device 120 or the vehicle user interface 1608, or an audible alert (e.g., a vocal message) may be transmitted through the speakers in the reader device 120 or the vehicle 1606.

If not done automatically, the operator 1602 may be prompted to obtain a current analyte level upon pairing the sensor control device 102 with the control module 1604. In some cases, the vehicle 1606 may be prevented from being operated until a current analyte level is obtained. If the current analyte levels are within safe limits, the computer system 1610 may allow operation of the vehicle 1606. In some aspects, and unless done automatically, the control module 1604 may prompt the operator 1602 to obtain additional current analyte levels after operating the vehicle 1606 for a predetermined period of time (e.g., after 1 hour, 2 hours, 5 hours, etc.).

In some embodiments, the control module 1604 may be configured to issue visual or audible recommendations or coaching to the operator 1602 that may help bring measured analyte levels back into safe ranges. In such embodiments, such visual or audible recommendations may prompt the user to take some action that could result in bringing analyte levels back into safe ranges. Moreover, in some embodiments, the operator 1602 may be able to communicate with the control module 1604 verbally by issuing verbal responses or commands. This may prove advantageous in helping prevent distracted operation of the vehicle 1606.

In some embodiments, settings of the control module 1604 may be customized by the operator 1602 to allow the user to make informed decisions once unsafe analyte levels have been detected and a visual or audible alert has been issued by the control module 1604. More specifically, in at least one embodiment, the control module 1604 may include a bypass feature that the operator 1602 might enable to allow the operator 1602 to operate the vehicle 1606 even when unsafe analyte levels have been measured. In such embodiments, the operator 1602 may operate the vehicle 1606 by acknowledging that the operator 1602 might be operating the vehicle 1606 in an impaired or unsafe health state.

In some embodiments, the computer system 1610 may be configured or otherwise programmed to calculate a predicted timeline when analyte levels of the operator 1602 may depart from a predetermined safe range or otherwise cross a predetermined threshold. In such embodiments, the control module 1604 may be configured to issue visual or audible alerts to the operator 1602 indicating approximately how much time the operator 1602 has before unsafe analyte levels may be reached and a potential unsafe medical condition may ensue. Multiple alerts may be provided to indicate when the operator has specific time increments remaining before unsafe analyte levels are reached. For example, visual or audible alerts may be issued when unsafe analyte levels will be reached within an hour, within a half hour, within 10 minutes, within 5 minutes, within 1 minute, and any time increment therebetween. Furthermore, a visual or audible alert may be issued once the analyte levels of the operator reach an unsafe level or cross a predetermined threshold.

In some embodiments, if unsafe analyte levels are measured while the operator 1602 is operating the vehicle 1606, the control module 1604 may be configured to issue one or more alerts (visual or audible) warning the operator 1602 of the unsafe analyte levels. In some cases, the volume of the stereo in the vehicle 1606 may be automatically lowered to enable the operator 1602 to hear an audible alert. In such embodiments, the control module 1604 may be configured to suggest one or more corrective actions to the operator 1602. Example corrective actions include, but are not limited to, slowing and stopping the vehicle 1606, locating and driving to a nearby convenience store or pharmacy, and locating a nearby hospital or medical facility. If the vehicle 1606 is an autonomous vehicle, and the current analyte levels place the operator 1602 in potentially dangerous conditions, the control module 1604 may automatically direct the vehicle 1606 to a medical facility for treatment. Alternatively, or in addition thereto, the control module 1604 may progressively reduce or restrict the speed of the vehicle 1606 when unsafe analyte levels are detected, thus forcing the operator 1602 to come to a stop and remedy the issue before continuing to operate the vehicle 1606.

The system 1600 may be useful in several different scenarios to protect the operator 1602 and/or those around the operator 1602 while driving. In some applications, the system 1600 may be incorporated voluntarily by the operator to detect impairment in real-time. In other applications, the system 1600 may be required by the owner of the vehicle 1606 to detect impairment of the operator 1602. In such applications, the owner of the vehicle 1606 may be a transport or trucking company. In yet other applications, the system 1600 may be legally imposed on the operator 1602 to detect impairment.

Embodiments disclosed herein include:

E. An analyte monitoring and vehicle control system that includes a sensor control device having a sensor that detects and monitors one or more analytes present within a body of an operator, and a control module in communication with the sensor control device and an electrical system of a vehicle, the control module including a computer system programmed to receive and process data provided by the sensor control device, wherein operation of the vehicle is controlled or disabled by the computer system when a real-time measured analyte level of the operator crosses a predetermined safe threshold.

F. A method that includes detecting and monitoring one or more analytes present within a body of an operator with a sensor control device having a sensor, receiving and processes data provided by the sensor control device with a control module in communication with the sensor control device and an electrical system of a vehicle; and controlling or disabling operation of the vehicle with a computer system of the control module when a real-time measured analyte level of the operator crosses a predetermined safe threshold.

Each of embodiments E and F may have one or more of the following additional elements in any combination: Element 1: wherein the sensor control device is coupled to the operator and the sensor is transcutaneously positioned beneath skin of the operator to detect and monitor the analytes present within a bodily fluid of the operator. Element 2: wherein the sensor control device comprises an ex vivo analyte sensor. Element 3: further comprising a reader device that receives the data from the sensor control device and transmits the data to the control module. Element 4: wherein the vehicle comprises a transportation vehicle selected from the group consisting of an automobile, an autonomous vehicle, a truck, a sport utility vehicle, an aircraft, a watercraft, a spacecraft, or any combination thereof. Element 5: wherein sensor control device pairs with the control module for communication upon the operator approaching the vehicle. Element 6: further comprising a vehicle user interface included in the vehicle and in communication with the control module. Element 7: wherein operation of the vehicle is disabled by disabling one or more critical systems of the vehicle, the critical systems being selected from the group consisting of an ignition system, a transmission system, a fuel system, and an energy supply system. Element 8: wherein operation of the vehicle is controlled by at least one of activating one or more non-critical systems of the vehicle, calling or sending a message to one or more emergency contacts, and progressively reducing a speed of the vehicle. Element 9: further comprising one or more proximity sensors installed on the vehicle to monitor an area of a driver's seat of the vehicle and detect a presence of the operator. Element 10: wherein the control module further includes a vehicle status detection module that detects the current status of the vehicle. Element 11: wherein the control module generates visual or audible alerts perceivable by the operator when the real-time measured analyte level of the operator falls outside of the predetermined safe threshold. Element 12: wherein the visual or audible alerts are generated at specific time increments before unsafe analyte levels are reached. Element 13: wherein the visual or audible alerts comprise one or more suggested corrective actions communicated to the operator. Element 14: wherein the control module includes a bypass feature allowing the operator to operate the vehicle when the real-time measured analyte level of the operator crosses the predetermined threshold.

Element 15: further comprising receiving the data from the sensor control device and transmitting the data to the control module with a reader device in communication with the sensor control device and the control module. Element 16: wherein disabling operation of the vehicle comprises disabling one or more critical systems of the vehicle, the critical systems being selected from the group consisting of an ignition system, a transmission system, a fuel system, and an energy supply system. Element 17: wherein controlling operation of the vehicle comprises at least one of activating one or more non-critical systems of the vehicle, calling or sending a message to one or more emergency contacts, and progressively reducing a speed of the vehicle. Element 18: further comprising monitoring an area of a driver's seat of the vehicle and detecting a presence of the operator with one or more proximity sensors installed on the vehicle. Element 19: further comprising detecting the current status of the vehicle with a vehicle status detection module included in the control module. Element 20: further comprising generating visual or audible alerts perceivable by the operator with the control module when the real-time measured analyte level of the operator crosses the predetermined threshold.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is:

1. An analyte sensor for detecting glucose and ketones in vivo, the sensor comprising:

a first working electrode, a second working electrode, a counter electrode, and a reference electrode;

a ketones-responsive active area disposed directly upon a surface of the first working electrode, the ketones-responsive active area comprising a first polymer and an enzyme system comprising nicotinamide adenine dinucleotide (NAD) and at least two enzymes that facilitate detection of ketones;

a glucose-responsive active area disposed upon a surface of the second working electrode, the glucose-responsive active area comprising a second polymer and a glucose-responsive enzyme;

a first membrane suitable for permitting sufficient inward diffusion of ketones and limiting outward diffusion of NAD, the first membrane disposed directly upon the ketones-responsive active area; and a second membrane suitable for permitting sufficient inward diffusion of glucose and ketones, the second membrane disposed upon the first membrane and upon the glucose-responsive active area, wherein the ketones-responsive active area is disposed closer to a distal end of the sensor than the glucose-responsive active area such that the first membrane is selectively disposed over the ketones-responsive active area relative to the glucose-responsive active area, and wherein the sensor is configured to be partially inserted into a user's skin such that a distal portion of the sensor is in contact with an interstitial fluid to detect glucose and ketones in vivo.

2. The analyte sensor of claim 1, wherein the ketones-responsive active area further comprises an electron transfer agent.

3. The analyte sensor of claim 2, wherein the electron transfer agent is covalently bonded to the first polymer.

4. The analyte sensor of claim 1, wherein one or more of the at least two enzymes is covalently bonded to the first polymer.

5. The analyte sensor of claim 1, wherein each of the at least two enzymes is covalently bonded to the first polymer.

6. The analyte sensor of claim 1, wherein the ketones-responsive active area further comprises albumin.

7. The analyte sensor of claim 6, wherein the albumin is covalently bonded to the first polymer.

8. The analyte sensor of claim 1, wherein the glucose-responsive enzyme is covalently bonded to the second polymer.

9. The analyte sensor of claim 1, wherein the glucose-responsive active area further comprises an electron transfer agent.

10. The analyte sensor of claim 9, wherein the electron transfer agent is covalently bonded to the second polymer.

11. The analyte sensor of claim 1, wherein the glucose-responsive enzyme is glucose oxidase or glucose dehydrogenase.

12. The analyte sensor of claim 1, wherein the enzyme system comprises β-hydroxybutyrate dehydrogenase and diaphorase.

13. The analyte sensor of claim 1, wherein the enzyme system comprises β-hydroxybutyrate dehydrogenase and nicotinamide adenine dinucleotide oxidase.

14. The analyte sensor of claim 1, wherein the first membrane comprises polyvinylpyridine.

15. The analyte sensor of claim 1, wherein the second membrane comprises polyvinylpyridine-co-styrene.

16. The analyte sensor of claim 1, wherein the sensor produces a first signal that increases linearly as a function of ketone concentrations from 0 mM to 10 mM over at least 3.5 hours.

17. The analyte sensor of claim 16, wherein the sensor produces a second signal that increases linearly as a function of glucose concentrations from 0 mM to 30 mM over at least 3.5 hours.

18. A method for detecting glucose and ketones in vivo, the method comprising:

exposing the analyte sensor of claim 1 to an interstitial fluid comprising glucose and ketones;

applying a potential to the first and second working electrodes;

obtaining a first signal at or above an oxidation-reduction potential of the first active area, the first signal being proportional to a concentration of ketones in the fluid;

obtaining a second signal at or above the oxidation-reduction potential of the second active area, the second signal being proportional to a concentration of glucose in the fluid;

correlating the first signal to the concentration of ketones in the fluid; and correlating the second signal to the concentration of glucose in the fluid.

* * * * *